United States Patent
Pouletty

(10) Patent No.: US 10,624,876 B2
(45) Date of Patent: Apr. 21, 2020

(54) DERIVATIVES OF INDOLE FOR THE TREATMENT OF ENDOMETRIOSIS

(71) Applicant: BIOKINESIS, Paris (FR)

(72) Inventor: Philippe Pouletty, Paris (FR)

(73) Assignee: BIOKINESIS, Paris (FR)

( * ) Notice: Subject to any disclaimer, the term of this patent is extended or adjusted under 35 U.S.C. 154(b) by 0 days.

(21) Appl. No.: 16/344,390

(22) PCT Filed: Oct. 23, 2017

(86) PCT No.: PCT/EP2017/076990
§ 371 (c)(1),
(2) Date: Apr. 24, 2019

(87) PCT Pub. No.: WO2018/077795
PCT Pub. Date: May 3, 2018

(65) Prior Publication Data
US 2019/0275000 A1 Sep. 12, 2019

(30) Foreign Application Priority Data
Oct. 24, 2016 (EP) ..................................... 16306389

(51) Int. Cl.
| | |
|---|---|
| *A61K 31/404* | (2006.01) |
| *A61P 15/00* | (2006.01) |
| *A61K 45/06* | (2006.01) |
| *C07D 405/14* | (2006.01) |
| *C07D 401/14* | (2006.01) |
| *C07D 209/18* | (2006.01) |
| *C07D 401/06* | (2006.01) |

(52) U.S. Cl.
CPC ............ *A61K 31/404* (2013.01); *A61K 45/06* (2013.01); *A61P 15/00* (2018.01); *C07D 209/18* (2013.01); *C07D 401/06* (2013.01); *C07D 401/14* (2013.01); *C07D 405/14* (2013.01)

(58) Field of Classification Search
CPC .............. A61K 31/404; A61K 31/4196; A61K 31/4439; C07D 405/14; C07D 401/14; C07D 209/18; A61P 15/02
See application file for complete search history.

(56) References Cited

U.S. PATENT DOCUMENTS

| | | |
|---|---|---|
| 9,643,923 B2 | 5/2017 | Bougeret et al. |
| 10,189,782 B2 | 1/2019 | Bougeret et al. |
| 2019/0169124 A1 | 6/2019 | Bougeret et al. |

FOREIGN PATENT DOCUMENTS

| | | |
|---|---|---|
| WO | WO 01/98299 | 12/2001 |
| WO | WO 2007/106236 | 9/2007 |
| WO | WO 2010/150211 | 12/2010 |
| WO | WO 2014/086964 | 6/2014 |

OTHER PUBLICATIONS

Demirkiran, F. "Is endometriosis a preneoplastic condition?" *Women's Health*, 2015, pp. 701-703, vol. 11, No. 5.
(Continued)

*Primary Examiner* — Angela C Brown-Pettigrew
(74) *Attorney, Agent, or Firm* — Saliwanchik, Lloyd & Eisenchenk

(57) ABSTRACT

The present invention relates to compounds of formula (I) and pharmaceutical compositions comprising such compounds, for use for treating and/or preventing endometriosis.

14 Claims, 1 Drawing Sheet

(56) References Cited

OTHER PUBLICATIONS

Figure 1:
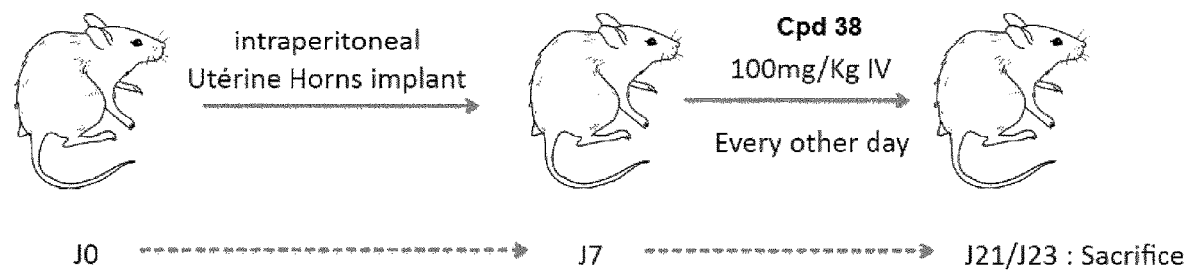

Kvaskoff, M. et al. "Endometriosis: a high-risk population for major chronic diseases?" *Human Reproduction Update*, 2015, pp. 500-516, vol. 21, No. 4.
Written Opinion in International Application No. PCT/EP2017/076990, dated Dec. 4, 2017, pp. 1-7.
Tcherniuk. S. et al. "Relocation of Aurora B and Survivin from Centromeres to the Central Spindle Impaired by a Kinesin-Specific MKLP-2 Inhibitor" *Angew. Chem. Int. Ed.*, 2010, pp. 8228-8231, vol. 49.
Dolusic, E. et al. "Tryptophan 2,3-Dioxygenase (TDO) Inhibitors. 3-(2-(Pyridyl)ethenyl)indoles as Potential Anticancer Immunomodulators" *Journal of Medicinal Chemistry*, 2011, pp. 5320-5334, vol. 54.
Tarleton, M. et al. "Cytotoxic 2-phenyacrylnitriles, the importance of the cyanide moiety and discovery of potent broad spectrum cytotoxic agents" *European Journal of Medicinal Chemistry*, 2012, pp. 65-73, vol. 57.
Ettmayer, P. et al. "Lessons Learned from Marketed and Investigational Prodrugs" *Journal of Medical Chemistry*, 2004, pp. 2393-2404, vol. 47, No. 10.
Jordan, V. C. "Tamoxifen: a most unlikely pioneering medicine" *Nature Reviews Drug Discovery*, Mar. 2003, pp. 205-213, vol. 2.
Stella, V. J. "Prodrugs as therapeutics" *Expert Opin. Ther. Patents*, 2004, pp. 277-280, vol. 47, No. 3.
Testa, B. "Prodrug research: futile or fertile?" *Biochemical Pharmacology*, 2004, pp. 2097-2106, vol. 68.

DERIVATIVES OF INDOLE FOR THE TREATMENT OF ENDOMETRIOSIS

CROSS-REFERENCE TO RELATED APPLICATION

This application is the U.S. national stage application of International Patent Application No. PCT/EP2017/076990, filed Oct. 23, 2017.

FIELD OF THE INVENTION

The present invention relates to medicinal field, and more particularly to the use of derivatives of indoles to treat endometriosis.

BACKGROUND OF THE INVENTION

Endometriosis is a hormone-dependent inflammatory disease that results in the presence of endometrium in the peritoneal cavity. The endometriosis lesions can be superficial or deep and can develop ovarian cysts (endometriomas). The mechanism of formation of such lesions is twofold. Firstly, the eutopic endometrial cells flow back into the peritoneal cavity through the tubes in each menstruation, then these cells, once in the peritoneal cavity, will adhere and invade the peritoneum, proliferate, thereby forming lesions. The proliferation of ectopic endometriotic lesions depends on hormonal factors, particularly local and systemic production of estradiol, and also on the local inflammatory response in the peritoneum and production of trophic factors (cytokines, chemokines, angiogenic factors, prostaglandins) for lesions.

Many molecules that could block the proliferation of endometriosis cells are currently under development. These molecules inhibit the proliferation by acting on the hormonal level and blocking the proproliferative effect of estradiol (aromatase inhibitor or receptors to estradiol, progestins), or by acting on the inflammatory component (antioxidant, prostaglandin inhibitor or pro-inflammatory cytokines), or by blocking intrinsic mitogenic signals endometriotic cells induced by the inflammatory response by inhibiting the MAPK or the mTOR-Akt pathway activated in these cells.

However, it remains a need to explore and understand such mechanism and, therefore, a need to develop new molecules to be applied in efficient treatments for treating and/or preventing endometriosis.

SUMMARY OF THE INVENTION

In this context, the inventors have surprisingly demonstrated that indoles derivatives disclosed by WO 2010/150211 and WO 2014/086964 for treating cancer thanks to their MKLP2 inhibitor properties, could also be used in treatments for treating endometriosis. More particularly, the inventors have demonstrated that compounds as disclosed in the present application reduced intraperitoneal implant volume and weight.

The present invention relates to compounds of formula (I):

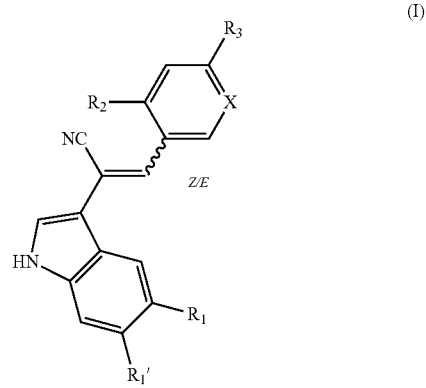

wherein:
X represents a nitrogen atom, a C—CN unit or a $N^+$—$O^-$ unit, preferably a nitrogen atom or a C—CN unit;
$R_1$ and $R_1'$ represent independently H, a halogen, a hydroxy, an amino, or a ($C_1$-$C_6$)alkoxy group, optionally substituted by a carboxylic group or one —$NR_{11}R_{12}$ unit wherein $R_{11}$ and $R_{12}$ represent H or a ($C_1$-$C_6$)alkyl group or $R_{11}$ and $R_{12}$ taken together form a 3- to 7-membered ring optionally interrupted by one or several heteroatoms, preferably a ($C_1$-$C_3$)alkoxy group;
$R_2$ represents:
a radical ($C_1$-$C_3$)alkyl, ($C_1$-$C_6$)alkoxy, ($C_3$-$C_6$)cycloalkoxy, aryloxy, heteroaryloxy, ($C_1$-$C_6$)alkyl-aryloxy, ($C_1$-$C_6$)alkyl-heteroaryloxy, said radicals being optionally substituted by at least one halogen, or a radical thio-($C_1$-$C_6$)alkyl, thio-aryl, thio-heteroaryl, thio-($C_1$-$C_6$)alkyl-aryl or thio-($C_1$-$C_6$)-alkyl-heteroaryl, said radicals being optionally substituted by at least one halogen or by a ($C_1$-$C_6$)alkoxy group,
a —$NR_4R_5$ unit, a O—($C_1$-$C_6$)alkyl-$NR_4R_5$ unit or a S—($C_1$-$C_6$)alkyl-$NR_4R_5$ unit wherein $R_4$ and $R_5$ represent H, a ($C_1$-$C_6$)alkyl group, or $R_4$ and $R_5$ taken together form a 3- to 7-membered ring, optionally interrupted by one or several heteroatoms, with the proviso that at least one among $R_4$ and $R_5$ is not H,
a $NHCOR_6$ unit wherein $R_6$ represents ($C_1$-$C_6$)alkyl group,
an aryl or heteroaryl group optionally substituted by at least one halogen, a trifluoromethyl group, or a ($C_1$-$C_3$)alkoxy group,
a halogen,
a hydroxy; and
$R_3$ represents a hydrogen, a ($C_1$-$C_3$)alkyl group, a ($C_1$-$C_3$)alkoxy group or a halogen, advantageously a fluorine;
and the compounds of formula (I), in which the nitrogen atom of the indole core is substituted by a group selected from the group consisting of a $COR_7$ and a $CO_2R_7$ group, wherein $R_7$ represents:
a ($C_1$-$C_6$)alkyl group, optionally substituted by at least a hydroxy group, a ($C_1$-$C_6$)alkyloxy group, a ($C_1$-$C_6$)$_n$polyalkyloxy group wherein n is 1<n<6, a phosphate or pyrophosphate group and salts or ($C_1$-$C_3$) alkyl ester thereof, a $R_8$ group, a —$NHCO_2R_8$ unit, a $COR_8$ group, or a $CO_2R_8$ group, wherein $R_8$ is:

a ($C_1$-$C_6$)alkyl group,
an aryl, a ($C_1$-$C_6$)alkylaryl, a heteroaryl,
a —$NR_9R_{10}$ unit wherein $R_9$ and $R_{10}$ represent a hydrogen, a ($C_1$-$C_6$)alkyl group, or $R_9$ and $R_{10}$ taken together form a 3- to 7-membered ring, optionally interrupted by one or several heteroatoms, and optionally the ring being substituted by at least one ($C_1$-$C_6$)alkyl group;
a NH—$NR_9R_{10}$ unit wherein $R_9$ and $R_{10}$ are such as defined above; or
a saturated heterocycle or a heteroaryl;
or one of its pharmaceutically acceptable salts;
for use for treating and/or preventing endometriosis.

In a particular embodiment, compounds having formula (I) as defined above are (Z)-isomers (formula Ia).

In another particular embodiment, compounds having formula (I) as defined above are (E)-isomers (formula Ib).

Particularly, the compound has formula (I), (Ia), or (Ib) as defined above with $R_1$' being H. More particularly, the compound has formula (I), (Ia), or (Ib) as defined above with $R_1$ being a halogen chosen among a bromine or a chlorine. Alternatively, $R_{1'}$ is a halogen chosen among a bromine, a chlorine, or a fluorine. In particular, $R_1$ is H and $R_{1'}$ is a halogen chosen among a bromine, a chlorine, or a fluorine Preferably, the compound has formula (I), (Ia), or (Ib) as defined above with $R_2$ being:
  a radical ($C_1$-$C_6$)alkoxy, phenoxy, said radicals being optionally substituted by at least one halogen;
  a halogen;
  a $R_4$—N—$R_5$ unit or a S—($C_1$-$C_6$)alkyl-$NR_4R_5$ unit, wherein $R_4$ and $R_5$ represent H, a ($C_1$-$C_6$)alkyl group with the proviso that at least one among $R_4$ and $R_5$ is not H,
  a $NHCOR_6$ unit wherein $R_6$ represents ($C_1$-$C_6$)alkyl group,
  a radical thio-($C_1$-$C_6$)alkyl, thio-aryl, thio-heteroaryl, thio-($C_1$-$C_6$)alkyl-aryl, said radicals being optionally substituted by at least one halogen or by a ($C_1$-$C_6$) alkoxy group;
  an aryl group optionally substituted by at least one halogen, or a trifluoromethyl group; or
  a heteroaryl group.

More preferably, the compound has formula (I), (Ia), or (Ib) as defined above with $R_2$ being:
  a radical ($C_1$-$C_6$)alkoxy selected from the group consisting of a methoxy group, an ethoxy group and an isopropoxy group, or a phenoxy group, optionally substituted by a fluorine, such as a trifluoromethyl;
  a halogen selected from the group consisting of a fluorine and a chlorine,
  a $R_4$—N—$R_5$ unit or a S—($C_1$-$C_6$)alkyl-$NR_4R_5$ unit wherein $R_4$ and $R_5$ represent a methyl or an ethyl group:
  a $NHCOR_6$ unit wherein $R_6$ represents a tert-butyl group;
  a radical selected in the group consisting of a thio-methyl group, a thio-ethyl group, a thio-benzyl group, a thio-pyridinyl group and a thio-phenyl group, optionally substituted by at least one fluorine or a trifluoromethyl group;
  a phenyl group optionally substituted by at least one bromine or a trifluoromethyl group; or
  a heteroaryl group selected from the group consisting of a furan or a triazol.

In a very particular aspect, the compound is selected from the group consisting of:
(Z)-3-(4-ethoxypyridin-3-yl)-2-(5-methoxy-1H-indol-3-yl)-acrylonitrile;
(Z)-2-(5-chloro-1H-indol-3-yl)-3-(4-chloropyridin-3-yl)-acrylonitrile;
(Z)-2-(5-bromo-1H-indol-3-yl)-3-(4-chloropyridin-3-yl)-acrylonitrile;
(Z)-2-(5-bromo-1H-indol-3-yl)-3-(4-methoxypyridin-3-yl)-acrylonitrile;
(E)-2-(5-bromo-1H-indol-3-yl)-3-(4-methoxypyridin-3-yl)-acrylonitrile;
(Z)-2-(5-chloro-1H-indol-3-yl)-3-(4-(dimethylamino)pyridin-3-yl)-acrylonitrile;
(Z)-2-(5-chloro-1H-indol-3-yl)-3-(4-dimethylamino)pyridine-3-yl)-acrylonitrile, hydrochloride;
(Z)-2-(5-bromo-1H-indol-3-yl)-3-(4-(dimethylamino)pyridin-3-yl)-acrylonitrile;
(Z)-2-(5-chloro-1H-indol-3-yl)-3-(4-methoxypyridin-3-yl)-acrylonitrile;
(E)-2-(5-chloro-1H-indol-3-yl)-3-(4-methoxypyridin-3-yl)-acrylonitrile;
(Z)-2-(5-chloro-1H-indol-3-yl)-3-(4-phenoxypyridin-3-yl)-acrylonitrile;
(Z)-2-(5-bromo-1H-indol-3-yl)-3-(4-phenoxypyridin-3-yl)-acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-ethoxypyridin-3-yl)-acrylonitrile;
(Z)-2-(5-bromo-1H-indol-3-yl)-3-(4-isopropoxypyridin-3-yl)-acrylonitrile;
(Z)-2-(5-bromo-1H-indol-3-yl)-3-(4-(methylthio)pyridin-3-yl)-acrylonitrile;
(Z)-2-(5-bromo-1H-indol-3-yl)-3-(4-(ethylthio)pyridin-3-yl)-acrylonitrile;
(Z)-2-(5-bromo-1H-indol-3-yl)-3-(4-(3-bromophenyl)pyridin-3-yl)-acrylonitrile;
(Z)-3-(4-(3-bromophenyl)pyridin-3-yl)-2-(5-chloro-1H-indol-3-yl)-acrylonitrile;
(Z)-2-(5-bromo-1H-indol-3-yl)-3-(4-(phenylthio)pyridin-3-yl)-acrylonitrile;
(Z)-3-(4-(benzylthio)pyridin-3-yl)-2-(5-bromo-1H-indol-3-yl)-acrylonitrile;
(Z)-2-(5-bromo-1H-indol-3-yl)-3-(4-(3,4-dimethoxy)thio)pyridin-3-yl)-acrylonitrile;
(Z)-2-(5-bromo-1H-indol-3-yl)-3-(4-(4-fluorophenoxy)pyridin-3-yl)-acrylonitrile;
(Z)-2-(5-chloro-1H-indol-3-yl)-3-(4-(4-fluorophenoxy)pyridin-3-yl)-acrylonitrile;
(Z)-2-(5-bromo-1H-indol-3-yl)-3-(4-(diethylamino)pyridin-3-yl)-acrylonitrile;
(Z)-2-(5-bromo-1H-indol-3-yl)-3-(4-(4-(trifluoromethyl)phenyl)pyridin-3-yl)-acrylonitrile;
(Z)-2-(5-chloro-1H-indol-3-yl)-3-(4-(4-(trifluoromethyl)phenyl)pyridin-3-yl)-acrylonitrile;
(Z)-2-(5-chloro-1H-indol-3-yl)-3-(4-((4-fluorophenyl)thio)pyridin-3-yl)-acrylonitrile;
(Z)-2-(5-bromo-1H-indol-3-yl)-3-(4-((4-fluorophenyl)thio)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)pyridin-3-yl)-acrylonitrile;
(Z)-2-(5-bromo-1H-indol-3-yl)-3-(4-(pyridine-2-ylthio)pyridin-3-yl)-acrylonitrile;
(Z)-3-(4-(1H-1,2,4-triazol-1-yl)pyridin-3-yl)-2-(5-bromo-1H-indol-3-yl)-acrylonitrile;
(Z)-3-(4-(1H-1,2,4-triazol-1-yl)pyridin-3-yl)-2-(5-chloro-1H-indol-3-yl)-acrylonitrile;

(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-2-(5-bromo-1H-indol-3-yl)-3-(4-(2-(dimethylamino)ethylthio)pyridin-3-yl)-acrylonitrile;
(Z)-3-(2-(5-bromo-1H-indol-3-yl)-2-cyanovinyl)-4-(4-fluorophenoxy)benzonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-3-(2-(5-chloro-1H-indol-3-yl)-2-cyanovinyl)-4-methoxybenzonitrile;
(Z)-3-(2-(5-chloro-1H-indol-3-yl)-2-cyanovinyl)-4-(dimethylamino)benzonitrile;
(Z)-3-(2-(5-chloro-1H-indol-3-yl)-2-cyanovinyl)-4-(ethylthio)benzonitrile;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
(Z)-3-(2-cyano-2-(6-methoxy-1H-indol-3-yl)vinyl)-4-methoxybenzonitrile;
(Z)-2-(1-acetyl-5-bromo-1H-indol-3-yl)-3-(4-methoxypyridin-3-yl)acrylonitrile;
(Z)-3-(2-(1-acetyl-5-bromo-1H-indol-3-yl)-2-cyanovinyl)-4-methoxybenzonitrile;
(Z)-2-(5-bromo-1-pivaloyl-1H-indol-3-yl)-3-(4-methoxypyridin-3-yl)acrylonitrile;
(Z)-3-(2-(5-bromo-1-pivaloyl-1H-indol-3-yl)-2-cyanovinyl)-4-methoxybenzonitrile;
(Z)-methyl 3-(5-bromo-3-(1-cyano-2-(4-methoxypyridin-3-yl)vinyl)-1H-indol-1-yl)-3-oxopropanoate;
(Z)-2-(5-bromo-1-(2-(dimethylamino)acetyl)-1H-indol-3-yl)-3-(4-methoxypyridin-3-yl)acrylonitrile:
(Z)-2-(4-methylpiperazin-1-yl)ethyl 5-bromo-3-(1-cyano-2-(4-methoxypyridin-3-yl)vinyl)-1H-indole-1-carboxylate;
((Z)-3-(2-(5-bromo-1-(2-(dimethylamino)acetyl)-1H-indol-3-yl)-2-cyanovinyl)-4-methoxybenzonitrile;
(Z)-tert-butyl 5-bromo-3-(1-cyano-2-(5-cyano-2-methoxyphenyl)vinyl)-1H-indole-1-carboxylate;
(R,Z)-benzyl-4-(5-bromo-3-(1-cyano-2-(5-cyano-2-methoxyphenyl)vinyl)-1H-indol-1-yl)-2-(tert-butoxycarbonylamino)-4-oxobutanoate;
(R,Z)-tert-butyl-5-(5-bromo-3-(1-cyano-2-(5-cyano-2-methoxyphenyl)vinyl)-1H-indol-1-yl)-2-(tert-butoxycarbonylamino)-5-oxopentanoate;
(R,Z)-benzyl-2-amino-4-(5-bromo-3-(1-cyano-2-(5-cyano-2-methoxyphenyl)vinyl)-1H-indol-1-yl)-4-oxobutanoate;
(Z)-3-(2-(5-bromo-1-(2-(4-methylpiperazin-1-yl)acetyl)-1H-indol-3-yl)-2-cyanovinyl)-4-methoxybenzonitrile;
(Z)-3-(2-(5-bromo-1-(2-(4-methylpiperazin-1-yl)acetyl)-1H-indol-3-yl)-2-cyanovinyl)-4-methoxybenzonitrile hydrochloride;
(S,Z)-3-(2-(1-(3-aminobutanoyl)-5-bromo-1H-indol-3-yl)-2-cyanovinyl)-4-methoxybenzonitrile hydrochloride;
(Z)-3-(2-(1-(2-aminoacetyl)-5-bromo-1H-indol-3-yl)-2-cyanovinyl)-4-methoxybenzonitrile hydrochloride;
(Z)-3-(2-(5-bromo-1-(2-(piperazin-1-yl)acetyl)-1H-indol-3-yl)-2-cyanovinyl)-4-methoxybenzonitrile hydrochloride;
(Z)-3-(2-(5-bromo-1-(2-(2-(2-methoxyethoxy)ethoxy)acetyl)-1H-indol-3-yl)-2-cyanovinyl)-4-methoxybenzonitrile;
(S,Z)-3-(2-(1-(2-amino-3-hydroxypropanoyl)-5-bromo-1H-indol-3-yl)-2-cyanovinyl)-4-methoxybenzonitrile hydrochloride;
(Z)-3-(2-(5-bromo-1-(5-oxopyrrolidine-2-carbonyl)-1H-indol-3-yl)-2-cyanovinyl)-4-methoxybenzonitrile;
(R,Z)-3-(2-(5-bromo-1-(2,6-diaminohexanoyl)-1H-indol-3-yl)-2-cyanovinyl)-4-methoxybenzonitrile dihydrochloride;
(Z)-3-(5-bromo-3-(1-cyano-2-(5-cyano-2-methoxyphenyl)vinyl)-1H-indol-1-yl)-3-oxopropyl dihydrogen phosphate;
(Z)-2-(1H-indol-3-yl)-3-pyridin-3-yl-acrylonitrile;
(Z)-2-(5-methoxy-1H-indol-3-yl)-3-pyridin-3-yl-acrylonitrile;
(Z)-2-(5-ethoxy-1H-indol-3-yl)-3-pyridin-3-yl-acrylonitrile;
(Z)-2-(5-isopropoxy-1H-indol-3-yl)-3-pyridin-3-yl-acrylonitrile;
(Z)-2-(5-chloro-1H-indol-3-yl)-3-pyridin-3-yl-acrylonitrile;
(Z)-2-(5-fluoro-1H-indol-3-yl)-3-pyridin-3-yl-acrylonitrile;
(Z)-2-(6-methoxy-1H-indol-3-yl)-3-pyridin-3-yl-acrylonitrile;
(Z)-3-(6-fluoropyridin-3-yl)-2-(5-methoxy-1H-indol-3-yl)-acrylonitrile;
(Z)-2-(5-hydroxy-1H-indol-3-yl)-3-pyridin-3-yl-acrylonitrile;
(Z)-3-[2-cyano-2-(5-methoxy-1H-indol-3-yl)-vinyl]-benzonitrile;
(Z)-2-(5-methoxy-1H-indol-3-yl)-3-(4-methyl-pyridin-3-yl)-acrylonitrile;
(Z)-2-(5-bromo-1H-indol-3-yl)-3-pyridin-3-yl-acrylonitrile;
(Z)-2-(5-amino-1H-indol-3-yl)-3-pyridin-3-yl-acrylonitrile;
(Z)-3-(4-chloro-pyridin-3-yl)-2-(5-methoxy-1H-indol-3-yl)-acrylonitrile;
(Z)-3-(6-chloro-pyridin-3-yl)-2-(5-methoxy-1H-indol-3-yl)-acrylonitrile;
(Z)-3-(6-methoxy-pyridin-3-yl)-2-(5-methoxy-1H-indol-3-yl)-acrylonitrile;
(Z)-2-(5-methoxy-1H-indol-3-yl)-3-(6-methyl-pyridin-3-yl)-acrylonitrile;
(Z)-3-[2-cyano-2-(5-hydroxy-1H-indol-3-yl)-vinyl]-benzonitrile;
and their pharmaceutically acceptable salts.

More preferably, the compound is selected from the group consisting of:
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
and their pharmaceutically acceptable salts.

The present invention further relates to a pharmaceutical composition comprising as an active ingredient one compound of the formula (I) as defined above, for use for treating and/or preventing endometriosis.

Optionally, the pharmaceutical composition of the present invention further comprises an additional anti-endometriosis drug, preferably selected from the group consisting of non-steroidal anti-inflammatory drugs (NSAIDs), opioids, hormonal contraceptives drugs, growth factor inhibitors, endogenous angiogenesis inhibitors, fumagillin analogues, statins, cyclo-oxygenase-2 inhibitors, phytochemical compounds, immunomodulators, dopamine agonists, peroxisome proliferator-activated receptor agonists, progestins, danazol, and gonadotropin-releasing hormone agonists.

In addition, the present invention relates to a kit comprising (a) a compound of the present invention; and (b) an additional anti-endometriosis drug as a combined preparation for simultaneous, separate or sequential use in the treatment of endometriosis.

DETAILED DESCRIPTION OF THE INVENTION

The inventors identified a class of derivatives of indoles of the formula (I):

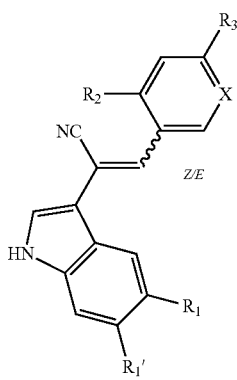

(I)

presenting a therapeutic interest, for treating endometriosis.

Accordingly, the present invention relates to compound of formula (I):

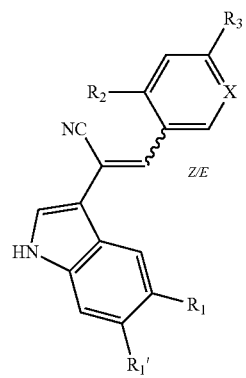

(I)

wherein:
X represents a nitrogen atom, a C—CN unit or a N$^+$—O$^-$ unit, preferably a nitrogen atom or a C—CN unit;
$R_1$ and $R_1'$ represent independently H, a halogen, a hydroxy, an amino or a ($C_1$-$C_6$)alkoxy group, optionally substituted by a carboxylic group or one —$NR_{11}R_{12}$ unit wherein $R_{11}$ and $R_{12}$ represent H or a ($C_1$-$C_6$)alkyl group or $R_{11}$ and $R_{12}$ taken together form a 3- to 7-membered ring optionally interrupted by one or several heteroatoms;
$R_2$ represents:
a radical ($C_1$-$C_3$)alkyl, ($C_1$-$C_6$)alkoxy, ($C_3$-$C_6$)cycloalkoxy, aryloxy, heteroaryloxy, ($C_1$-$C_6$)alkyl-aryloxy, ($C_1$-$C_6$)alkyl-heteroaryloxy, said radicals being optionally substituted by at least one halogen,
a hydroxy,
a halogen,
a —$NR_4R_5$ unit, a O—($C_1$-$C_6$)alkyl-$NR_4R_5$ unit or a S—($C_1$-$C_6$)alkyl-$NR_4R_5$ unit wherein $R_4$ and $R_5$ represent H or a ($C_1$-$C_6$)alkyl group, or $R_4$ and $R_5$ taken together form a 3- to 7-membered ring, optionally interrupted by one or several heteroatoms, with the proviso that at least one among $R_4$ and $R_5$ is not H,
a $NHCOR_6$ unit wherein $R_6$ represents ($C_1$-$C_6$)alkyl group,
a radical thio-($C_1$-$C_6$)alkyl, thio-aryl, thio-heteroaryl, thio-($C_1$-$C_6$)alkyl-aryl or thio-($C_1$-$C_6$)-alkyl-heteroaryl, said radicals being optionally substituted by at least one halogen or by a ($C_1$-$C_6$)alkoxy group,
an aryl group optionally substituted by at least one halogen, a trifluoromethyl group, or a ($C_1$-$C_3$)alkoxy group, or
a heteroaryl group, eventually substituted by a halogen, a trifluoromethyl group or a ($C_1$-$C_3$)alkoxy group; and
$R_3$ represents a hydrogen, a ($C_1$-$C_3$)alkyl group, a ($C_1$-$C_3$)alkoxy group or a halogen, advantageously a fluorine;
or one of its pharmaceutically acceptable salts; for use for treating and/or preventing endometriosis.

In a particular embodiment, when $R_1$ or $R_1'$ is a ($C_1$-$C_6$) alkoxy group, optionally substituted by one $R_{11}$—N—$R_{12}$ unit as above defined or a carboxylic group, then $R_2$ is not a halogen the compound of formula (I).

In a preferred embodiment, $R_1$ and $R_1'$ are such that one represents a halogen or a ($C_1$-$C_3$)alkoxy group, optionally substituted by a carboxylic group or one $R_{11}$—N—$R_{12}$ unit as above defined. In a more preferred embodiment, $R_1$ and $R_1'$ are such that one represents a halogen or a ($C_1$-$C_3$)alkoxy group.

The present invention also relates to prodrugs of the compounds disclosed in the present application for use for treating and/or preventing endometriosis, preferably prodrugs in which the nitrogen atom of the indole core is substituted. Accordingly, the present invention relates to prodrugs in which the nitrogen atom of the indole core is substituted by a group selected from the group consisting of a $COR_7$ and a $CO_2R_7$ group, wherein $R_7$ represents:
a ($C_1$-$C_6$)alkyl group, optionally substituted by at least a hydroxy group, a ($C_1$-$C_6$)alkyloxy group, a ($C_1$-$C_6$)$_n$polyalkyloxy group wherein n is 1<n<6, a phosphate or pyrophosphate group and salts or ($C_1$-$C_3$)alkyl ester thereof, a $R_8$ group, a —$NHCO_2R_8$ unit, a $COR_8$ group, or a $CO_2R_8$ group, wherein $R_8$ is:
a ($C_1$-$C_6$)alkyl group,
an aryl, a ($C_1$-$C_6$)alkylaryl, or a heteroaryl,
a $NR_9R_{10}$ unit wherein $R_9$ and $R_{10}$ represent a hydrogen, a ($C_1$-$C_6$)alkyl group, or $R_9$ and $R_{10}$ taken together form a 3- to 7-membered ring, optionally interrupted by one or several heteroatoms, and optionally the ring being substituted by at least one ($C_1$-$C_6$)alkyl group;

a NH—NR$_9$R$_{10}$ unit wherein R$_9$ and R$_{10}$ are such as defined above; or a saturated heterocycle or a heteroaryl.

In a particular embodiment, the present invention relates to compounds of formula (Ia):

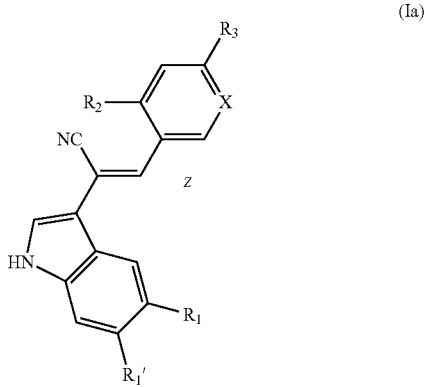

(Ia)

wherein X, R$_1$, R$_1'$, R$_2$, and R$_3$ are such as defined above for use for treating and/or preventing endometriosis. It also relates to prodrugs thereof as defined in the present document.

In another particular embodiment, the present invention relates to compounds of formula (Ib):

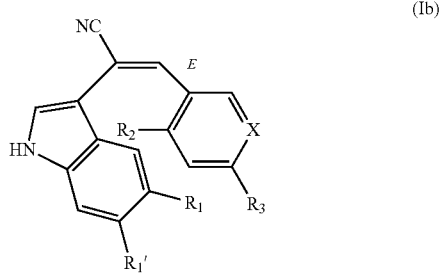

(Ib)

wherein X, R$_1$, R$_1'$, R$_2$, and R$_3$ are such as defined above for use for treating and/or preventing endometriosis. It also relates to prodrugs thereof as defined in the present document.

In another particular embodiment, the present invention relates to compounds of formula (II):

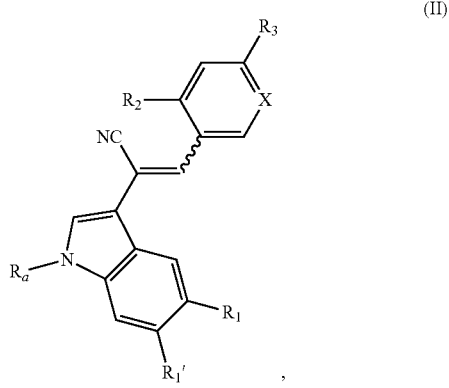

(II)

wherein X, R$_1$, R$_1'$, R$_2$, and R$_3$ are such as defined above, and R$_a$ is a group selected from the group consisting of a COR$_7$ and a CO$_2$R$_7$ group, wherein R$_7$ represents:

a (C$_1$-C$_6$)alkyl group, optionally substituted by at least a hydroxy group, a (C$_1$-C$_6$)alkyloxy group, a (C$_1$-C$_6$)$_n$polyalkyloxy group wherein n is 1<n<6, a phosphate or pyrophosphate group and salts or (C$_1$-C$_3$) alkyl ester thereof, a R$_8$ group, a —NHCO$_2$R$_8$ unit, a COR$_8$ group, or a CO$_2$R$_8$ group, wherein R$_8$ is:

a (C$_1$-C$_6$)alkyl group, an aryl, a (C$_1$-C$_6$)alkylaryl, or a heteroaryl, a NR$_9$R$_{10}$ unit wherein R$_9$ and R$_{10}$ represent a hydrogen, a (C$_1$-C$_6$)alkyl group, or R$_9$ and R$_{10}$ taken together form a 3- to 7-membered ring, optionally interrupted by one or several heteroatoms, and optionally the ring being substituted by at least one (C$_1$-C$_6$)alkyl group;

a NH—NR$_9$R$_{10}$ unit wherein R$_9$ and R$_{10}$ are such as defined above; or a saturated heterocycle or a heteroaryl;

or one of its pharmaceutically acceptable salts, for use for treating and/or preventing endometriosis.

According to the present invention, the terms below have the following meanings: The terms mentioned herein with prefixes such as for example C$_1$-C$_3$ or C$_1$-C$_6$ can also be used with lower numbers of carbon atoms such as C$_1$-C$_2$ or C$_1$-C$_5$. If, for example, the term C$_1$-C$_3$ is used, it means that the corresponding hydrocarbon chain may comprise from 1 to 3 carbon atoms, especially 1, 2 or 3 carbon atoms. If, for example, the term C$_1$-C$_6$ is used, it means that the corresponding hydrocarbon chain may comprise from 1 to 6 carbon atoms, especially 1, 2, 3, 4, 5 or 6 carbon atoms.

The term "alkyl" refers to a saturated, linear or branched aliphatic group. The term "(C$_1$-C$_3$)alkyl" more specifically means methyl (also called "Me"), ethyl (also called "Et"), propyl, or isopropyl, the term "(C$_1$-C$_6$)alkyl" more specifically means methyl, ethyl, propyl, isopropyl, butyl, isobutyl, tert-butyl or propyl, pentyl or hexyl.

The term "halogen" corresponds to a fluorine, chlorine, bromine, or iodine atom, preferably a fluorine, chlorine or bromine, and more preferably a chlorine or a bromine.

The term "alkoxy" or "alkyloxy" corresponds to the alkyl group defined hereinabove bonded to the molecule by an —O— (ether) bond. (C$_1$-C$_3$)alkoxy includes methoxy, ethoxy, propyloxy, and isopropyloxy. (C$_1$-C$_6$)alkoxy includes methoxy, ethoxy, propyloxy, isopropyloxy, butyloxy, isobutyloxy, tert-butyloxy, pentyloxy and hexyloxy. The term (C$_1$-C$_6$)$_n$polyalkyloxy corresponds to n (C$_1$-C$_6$) alkyloxy bounded thereby forming a linear poly(C$_1$-C$_6$) alkylene glycol chain, preferably a linear polyethylene glycol chain. Preferably, n is 1<n<6.

The term "thio" corresponds to the alkyl group defined hereinabove bounded to the molecule by a —S— (thioether) bound. Thio-(C$_1$-C$_6$)alkyl group includes thio-methyl, thio-ethyl, thio-propyl, thio-butyl, thio-pentyl and thio-hexyl.

The term "aryl" is mono- or bi-cyclic aromatic hydrocarbons having from 6 to 12 carbon atoms, optionally substituted. Aryl may be a phenyl (also called "Ph"), biphenyl or naphthyl. In a preferred embodiment, the aryl is a phenyl.

The term "heteroaryl" as used herein corresponds to an aromatic, mono- or poly-cyclic group comprising between 5 and 14 atoms and comprising at least one heteroatom such as nitrogen, oxygen or sulphur atom. Examples of such mono- and poly-cyclic heteroaryl group may be: pyridyl, dihydroypyridyl, thiazolyl, thiophenyl, furanyl, azocinyl, pyranyl, pyrrolyl, pyrazolyl, imidazolyl, triazolyl, tetrazolyl, benzofuranyl, thianaphthalenyl, indolyl, indolenyl, quinolinyl, isoquinolinyl, benzimidazolyl, pyrrolinyl, tetrahydroquinolinyl, tetrahydroisoquinolinyl, triazinyl, 6H-1,2,5-thiadiazinyl, 2H,6H-1,5,2-dithiazinyl, thianthrenyl, isobenzofuranyl, chromenyl, xanthenyl, phenoxanthinyl, 2H-pyrrolyl, isothiazolyl, isoxazolyl, pyrazinyl, pyridazinyl, indolizinyl, isoindolyl, 3H-indolyl, 1-Hindazolyl, purinyl, 4H-quinolizinyl, phtalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzisoxazolyl, oxindolyl, benzoxazolinyl, benzothienyl, benzothiazolyl, isatinyl, dihydropyridyl, pyrimidinyl, pyrazinyl, s-triazinyl, oxazolyl, thiofuranyl. In a preferred embodiment heteroaryl is an aromatic monocyclic comprising 5 or 6 atoms and comprising at least one heteroatom such as nitrogen, oxygen or sulphur atom. Preferably, heteroaryl is pyridyl, thiazolyl, furanyl, pyranyl, pyrrolyl, imidazolyl, tetrazolyl, benzofuranyl, pyrrolinyl, triazinyl, pyrazinyl, pyridazinyl, triazolyl or tetrazolyl. More preferably, heteroaryl is furanyl or triazolyl.

$(C_3-C_6)$cycloalkoxy includes cyclopropoxy, cyclobutoxy, cyclopentoxy and cyclohexoxy, $(C_3-C_6)$cycloalkyl includes cyclopropyl, cyclobutyl, cyclopentyl and cyclohexyl.

The term "saturated heterocycle" as used herein corresponds to a non-aromatic mono- or poly-cyclic group comprising between 5 and 14 atoms and comprising at least one heteroatom such as nitrogen, oxygen or sulphur atom. Examples of such heterocycle may be cyclohexanyl, tetrahydrofuranyl, pyrrolidinyl, piperidinyl, dioxanyl, morpholinyl, piperazinyl. Particularly, the saturated heterocycle may be substituted, for instance by a ketone. More preferably, the saturated heterocycle is oxopyrrolidinyl.

The expression "substituted by at least" means that the radical is substituted by one or several groups of the list.

By "$R_x$—N—$R_y$" is intended to refer to a unit "—$NR_xR_y$".

The terms "carboxylic" "Boc" and "Cbz" respectively correspond to the following groups "—COOH", "—C(=O)—O—C(CH_3)_3" and ""—C(=O)—O—CH_2_Phenyl".

The pharmaceutically acceptable salts include inorganic as well as organic acids salts. Representative examples of suitable inorganic acids include hydrochloric, hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. Further examples of pharmaceutically acceptable inorganic or organic acid addition salts include the pharmaceutically acceptable salts listed in J. Pharm. Sci. 1977, 66, 2, and in Handbook of Pharmaceutical Salts: Properties, Selection, and Use edited by P. Heinrich Stahl and Camille G. Wermuth 2002. In a preferred embodiment, the salt is selected from the group consisting of maleate, chlorhydrate, bromhydrate, and methanesulfonate.

In a preferred embodiment, $R_1$ and $R_1'$ are such that one is H and the other represents a halogen or a $(C_1-C_6)$alkoxy group, optionally substituted by one $R_{11}$—N—$R_{12}$ unit as above defined, or a carboxylic group. Preferably, $R_1'$ or $R_1$ represents a halogen, typically, a bromine, a chlorine or a fluorine, advantageously a bromine or a chlorine, more specifically a bromine. Alternatively, $R_1'$ or $R_1$ represent a $(C_1-C_6)$alkoxy group optionally substituted by one $R_{11}$—N—$R_{12}$ unit as above defined or a carboxylic group, preferably a $(C_1-C_3)$alkoxy group optionally substituted by one $R_{11}$—N—$R_{12}$ unit as above defined or a carboxylic group, more preferably a $(C_1-C_3)$alkoxy group, advantageously a methoxy, an ethoxy or an isopropoxy, more advantageously a methoxy. $R_{11}$ and $R_{12}$ are such as defined above and preferably represent a $(C_1-C_3)$alkyl group, and more preferably, a methyl or an ethyl group.

In a preferred embodiment, $R_1'$ is H. In another preferred embodiment, $R_1'$ is a halogen chosen among a bromine, a chlorine, or a fluorine, and $R_1$ is H.

Particularly, $R_2$ represents:
  a radical $(C_1-C_6)$alkoxy or phenoxy, said radicals being optionally substituted by at least one halogen, preferably a bromine, a chlorine or a fluorine, more preferably a fluorine, such as a trifluoromethyl;
  a halogen, preferably a bromine, a chlorine, or a fluorine, more preferably a bromine or a chlorine;
  a $R_4$—N—$R_5$ unit or a S—$(C_1-C_6)$alkyl-$NR_4R_5$ unit, wherein $R_4$ and $R_5$ represent H or a $(C_1-C_6)$alkyl group, with the proviso that at least one among $R_4$ and $R_5$ is not H,
  a $NHCOR_6$ unit wherein $R_6$ represents $(C_1-C_6)$alkyl group, advantageously a methyl, an ethyl or a tert-butyl;
  a radical thio-$(C_1-C_6)$alkyl, thio-aryl, thio-heteroaryl, thio-$(C_1-C_6)$alkyl-aryl, said radicals being optionally substituted by at least one halogen, a trifluoromethyl, or by a $(C_1-C_6)$alkoxy group;
  an aryl group optionally substituted by at least one halogen, or a trifluoromethyl group; or
  a heteroaryl group, advantageously a furan, a triazol, a pyridin, a thiazol, a pyran, a pyrrol, an imidazol, a tetrazol, a benzofuran, triazinyl, pyrazinyl, a pyridazin, or a tetrazol.

In a particular embodiment in which $R_2$ represents a radical $(C_1-C_6)$alkoxy, the radical $(C_1-C_6)$alkoxy is selected from the group consisting of a methoxy, propoxy, butoxy, pentoxy and hexoxy.

Preferably, $R_2$ represents:
  a radical $(C_1-C_6)$alkoxy selected from the group consisting of a methoxy group, an ethoxy group, and an isopropoxy group, preferably selected from the group consisting of a methoxy group, and an isopropoxy group, or a phenoxy group, optionally substituted by a fluorine, such as a trifluoromethyl;
  a halogen selected from the group consisting of a fluorine and a chlorine,
  a $R_4$—N—$R_5$ unit or a S—$(C_1-C_6)$alkyl-$NR_4R_5$ unit wherein $R_4$ and $R_5$ represent a methyl or an ethyl group:
  a radical selected from the group consisting of a thiomethyl group, a thio-ethyl group, a thio-benzyl group, a thio-pyridinyl group and a thio-phenyl group, optionally substituted by at least one fluorine or a trifluoromethyl group;
  a phenyl group optionally substituted by at least one bromine or a trifluoromethyl group; or
  a heteroaryl group selected from the group consisting of a furan or a triazol.

Particularly, $R_3$ represents a hydrogen, a $(C_1-C_3)$alkyl group, preferably a methyl, an ethyl or an isopropyl; a $(C_1-C_3)$alkoxy group, preferably a methoxy, an ethoxy or an isopropoxy; or a halogen, advantageously a fluorine. Preferably, $R_3$ is H, methoxy or fluorine. More preferably, $R_3$ is H.

In a particular embodiment of the invention:
  $R_1'$ or $R_1$ represents a halogen, typically a bromine, a chlorine or a fluorine, advantageously a bromine or a chlorine, more specifically a bromine. In a particular embodiment, $R_1'$ is H. Alternatively $R_1'$ is a halogen chosen among a bromine, a chlorine, or a fluorine, and $R_1$ is H.

$R_2$ represents:
- a radical $(C_1-C_6)$alkoxy, preferably a methoxy, an ethoxy, or an isopropoxy, more preferably a methoxy, or isopropoxy group, and a phenoxy optionally substituted by a fluorine, such as a trifluoromethyl; or
- a halogen, advantageously a fluorine and a chlorine, more advantageously a chlorine; or
- a $R_4$—N—$R_5$ unit or a S—$(C_1-C_6)$alkyl-$NR_4R_5$ unit wherein $R_4$ and $R_5$ represent a $(C_1-C_6)$alkyl group, preferably a methyl or an ethyl group; or
- a radical thio-$(C_1-C_6)$alkyl, preferably a thio-methyl or a thio-ethyl; a radical thio-aryl, preferably a thio-phenyl; a radical thio-heteroaryl, preferably, a thio-pyridinyl; or a radical thio-$(C_1-C_6)$alkyl-aryl, preferably a thio-benzyl; said radicals being optionally substituted by at least a halogen, preferably a fluorine, a trifluoromethyl, or by a $(C_1-C_6)$alkoxy group, preferably a methoxy, ethoxy, isopropoxy, more preferably a methoxy;
- a phenyl group optionally substituted by at least one halogene, preferably a bromine, or a trifluoromethyl group; or
- a heteroaryl group, preferably a furan, a triazol, a pyridin, a thiazol, a pyran, a pyrrol, an imidazol, a benzofuran, a triazol, or a tetrazol, and more preferably a furan or a triazol; and optionally, $R_3$ represents a hydrogen or a $(C_1-C_3)$alkyl group, preferably a methyl, an ethyl or an isopropyl; a $(C_1-C_3)$ alkoxy group, preferably a methoxy, an ethoxy or an isopropoxy; or a halogen, advantageously a fluorine. Preferably, $R_3$ is H, methoxy or fluorine.

More preferably, $R_3$ is H.

In another particular embodiment of the invention
$R_1'$ or $R_1$ represents a $(C_1-C_6)$alkoxy group optionally substituted by one $R_{11}$—N—$R_{12}$ unit as above defined or a carboxylic group, preferably a $(C_1-C_3)$alkoxy group optionally substituted by one $R_{11}$—N—$R_{12}$ unit as above defined, preferably wherein $R_4$ and $R_5$ represent a $(C_1-C_3)$alkyl group and more preferably a methyl or an ethyl group, or carboxylic group, more preferably a $(C_1-C_3)$alkoxy group, still more preferably a methoxy. Advantageously, $R_1'$ is H. Alternatively $R_1'$ is a halogen chosen among a bromine, a chlorine, or a fluorine, and $R_1$ is H. Optionally, $R_1'$ is a methoxy and $R_1$ is H;

$R_2$ represents:
- a radical $(C_1-C_6)$alkoxy, preferably a methoxy, an ethoxy or an isopropoxy, more preferably a methoxy or an ethoxy, still more preferably a methoxy; or a phenoxy group, optionally substituted by a fluorine, such as a trifluoromethyl; or
- a $R_4$—N—$R_5$ unit or a S—$(C_1-C_6)$alkyl-$NR_4R_5$ unit wherein $R_4$ and $R_5$ represent a $(C_1-C_6)$alkyl group, preferably a methyl or an ethyl group; or
- a radical thio-$(C_1-C_6)$alkyl, preferably, a thio-methyl or a thio-ethyl; a radical thio-aryl, preferably a thio-phenyl; a radical thio-heteroaryl, preferably, a thio-pyridinyl; or a radical thio-$(C_1-C_6)$alkyl-aryl, preferably a thio-benzyl; said radicals being optionally substituted by at least a halogen, preferably a fluorine, a trifluoromethyl, or by a $(C_1-C_6)$alkoxy group, preferably a methoxy, ethoxy, isopropoxy, more preferably a methoxy;
- a phenyl group optionally substituted by at least one halogene, preferably a bromine, or a trifluoromethyl group; or
- a heteroaryl group, preferably a furan, a triazol, a pyridin, a thiazol, a pyran, a pyrrol, an imidazol, a benzofuran, a pyridazin, or a tetrazol, and more preferably a furan or a triazol; and $R_3$ represents a hydrogen or a $(C_1-C_3)$alkyl group, preferably a methyl, an ethyl or an isopropyl; a $(C_1-C_3)$ alkoxy group, preferably a methoxy, an ethoxy or an isopropoxy; or a halogen, advantageously a fluorine. More preferably $R_3$ is H.

The present invention also relates to compounds of formula (II) for use as above defined. In a particular embodiment of the invention, $R_a$ is a group selected from the group consisting of a $COR_7$ and a $CO_2R_7$ group and $R_7$ represents a $(C_1-C_6)$alkyl group, preferably a methyl group or a tert-butyl group.

In another particular embodiment, $R_a$ is a group selected from the group consisting of a $COR_7$ and a $CO_2R_7$ group and $R_7$ is a $(C_1-C_6)$alkyl group, preferably a methyl, ethyl, propyl group or tert-butyl group, optionally substituted by at least:
- a hydroxy group,
- a $(C_1-C_6)_n$polyalkyloxy group with n=3,
- a $R_8$ group, a —$NHCO_2R_8$ unit, a $COR_8$ group, or a $CO_2R_8$ group wherein $R_8$ is such as defined above. Preferably, $R_8$ is:
  - a $(C_1-C_6)$alkyl group, preferably a methyl or a tert-butyl group,
  - a $(C_1-C_6)$alkylaryl, preferably, a benzyl group,
  - a $NR_9R_{10}$ unit wherein $R_9$ and $R_{10}$ preferably represent a hydrogen, a methyl group or $R_9$ and $R_{10}$ taken together form piperazinyl ring, optionally substituted by a methyl group,
  - a phosphate or pyrophosphate group or a salt thereof, preferably a phosphate group.

In another particular embodiment, $R_7$ represents:
- a NH—$NR_9R_{10}$ unit wherein $R_9$ and $R_{10}$ are hydrogen, or
- a saturated heterocycle, preferably oxopyrrolidinyl.

In a preferred embodiment, $R_a$ is a group selected from the group consisting of a $COR_7$ and a $CO_2R_7$ group and $R_7$ represents a methyl or a tert-butyl group, a $(C_1-C_3)$alkyl substituted by at least one group selected from the group consisting of a $CO_2CH_3$, $N(CH_3)_2$, piperazinyl-$CH_3$, NHBoc, Cbz, Boc, $NH_2$ and phosphate group.

Among the compounds according to the present invention, the following list of compounds may be cited:
- (Z)-3-(4-ethoxypyridin-3-yl)-2-(5-methoxy-1H-indol-3-yl)-acrylonitrile;
- (Z)-2-(5-chloro-1H-indol-3-yl)-3-(4-chloropyridin-3-yl)-acrylonitrile;
- (Z)-2-(5-bromo-1H-indol-3-yl)-3-(4-chloropyridin-3-yl)-acrylonitrile;
- (Z)-2-(5-bromo-1H-indol-3-yl)-3-(4-methoxypyridin-3-yl)-acrylonitrile;
- (E)-2-(5-bromo-1H-indol-3-yl)-3-(4-methoxypyridin-3-yl)-acrylonitrile;
- (Z)-2-(5-chloro-1H-indol-3-yl)-3-(4-(dimethylamino)pyridin-3-yl)-acrylonitrile;
- (Z)-2-(5-chloro-1H-indol-3-yl)-3-(4-dimethylamino)pyridine-3-yl)-acrylonitrile, hydrochloride;
- (Z)-2-(5-bromo-1H-indol-3-yl)-3-(4-(dimethylamino)pyridin-3-yl)-acrylonitrile;
- (Z)-2-(5-chloro-1H-indol-3-yl)-3-(4-methoxypyridin-3-yl)-acrylonitrile;

(E)-2-(5-chloro-1H-indol-3-yl)-3-(4-methoxypyridin-3-yl)-acrylonitrile;
(Z)-2-(5-chloro-1H-indol-3-yl)-3-(4-phenoxypyridin-3-yl)-acrylonitrile;
(Z)-2-(5-bromo-1H-indol-3-yl)-3-(4-phenoxypyridin-3-yl)-acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-ethoxypyridin-3-yl)-acrylonitrile;
(Z)-2-(5-bromo-1H-indol-3-yl)-3-(4-isopropoxypyridin-3-yl)-acrylonitrile;
(Z)-2-(5-bromo-1H-indol-3-yl)-3-(4-methylthio)pyridin-3-yl)-acrylonitrile;
(Z)-2-(5-bromo-1H-indol-3-yl)-3-(4-ethylthio)pyridin-3-yl)-acrylonitrile;
(Z)-2-(5-bromo-1H-indol-3-yl)-3-(4-(3-bromophenyl)pyridin-3-yl)-acrylonitrile;
(Z)-3-(4-(3-bromophenyl)pyridin-3-yl)-2-(5-chloro-1H-indol-3-yl)-acrylonitrile;
(Z)-2-(5-bromo-1H-indol-3-yl)-3-(4-(phenylthio)pyridin-3-yl)-acrylonitrile;
(Z)-3-(4-(benzylthio)pyridin-3-yl)-2-(5-bromo-1H-indol-3-yl)-acrylonitrile;
(Z)-2-(5-bromo-1H-indol-3-yl)-3-(4-(3,4-dimethoxy)thio)pyridin-3-yl)-acrylonitrile;
(Z)-2-(5-bromo-1H-indol-3-yl)-3-(4-(4-fluorophenoxy)pyridin-3-yl)-acrylonitrile;
(Z)-2-(5-chloro-1H-indol-3-yl)-3-(4-(4-fluorophenoxy)pyridin-3-yl)-acrylonitrile;
(Z)-2-(5-bromo-1H-indol-3-yl)-3-(4-(diethylamino)pyridin-3-yl)-acrylonitrile;
(Z)-2-(5-bromo-1H-indol-3-yl)-3-(4-(4-(trifluoromethyl)phenyl)pyridin-3-yl)-acrylonitrile;
(Z)-2-(5-chloro-1H-indol-3-yl)-3-(4-(4-(trifluoromethyl)phenyl)pyridin-3-yl)-acrylonitrile;
(Z)-2-(5-chloro-1H-indol-3-yl)-3-(4-((4-fluorophenyl)thio)pyridin-3-yl)-acrylonitrile;
(Z)-2-(5-bromo-1H-indol-3-yl)-3-(4-((4-fluorophenyl)thio)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)pyridin-3-yl)-acrylonitrile;
(Z)-2-(5-bromo-1H-indol-3-yl)-3-(4-(pyridine-2-ylthio)pyridin-3-yl)-acrylonitrile;
(Z)-3-(4-(1H-1,2,4-triazol-1-yl)pyridin-3-yl)-2-(5-bromo-1H-indol-3-yl)-acrylonitrile;
(Z)-3-(4-(1H-1,2,4-triazol-1-yl)pyridin-3-yl)-2-(5-chloro-1H-indol-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-2-(5-bromo-1H-indol-3-yl)-3-(4-(2-(dimethylamino)ethylthio)pyridin-3-yl)-acrylonitrile;
(Z)-3-(2-(5-bromo-1H-indol-3-yl)-2-cyanovinyl)-4-(4-fluorophenoxy)benzonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-3-(2-(5-chloro-1H-indol-3-yl)-2-cyanovinyl)-4-methoxybenzonitrile;
(Z)-3-(2-(5-chloro-1H-indol-3-yl)-2-cyanovinyl)-4-(dimethylamino)benzonitrile;
(Z)-3-(2-(5-chloro-1H-indol-3-yl)-2-cyanovinyl)-4-(ethylthio)benzonitrile;
(Z)-N-(3-(2-(5-bromo-1H-indol-3-yl)-2-cyanovinyl)pyridin-4-yl)pivalamide;
(Z)-N-(3-(2-(5-chloro-1H-indol-3-yl)-2-cyanovinyl)pyridin-4-yl)pivalamide;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-2-(5-chloro-1H-indol-3-yl)-3-(4-hydroxypyridin-3-yl)acrylonitrile;
(Z)-3-(2-(5-bromo-1H-indol-3-yl)-2-cyanovinyl)-4-hydroxybenzonitrile;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
(Z)-3-(2-cyano-2-(6-methoxy-1H-indol-3-yl)vinyl)-4-methoxybenzonitrile;
(Z)-2-(1-acetyl-5-bromo-1H-indol-3-yl)-3-(4-methoxypyridin-3-yl)acrylonitrile;
(Z)-3-(2-(1-acetyl-5-bromo-1H-indol-3-yl)-2-cyanovinyl)-4-methoxybenzonitrile;
(Z)-2-(5-bromo-1-pivaloyl-H-indol-3-yl)-3-(4-methoxypyridin-3-yl)acrylonitrile;
(Z)-3-(2-(5-bromo-1-pivaloyl-1H-indol-3-yl)-2-cyanovinyl)-4-methoxybenzonitrile;
(Z)-methyl 3-(5-bromo-3-(1-cyano-2-(4-methoxypyridin-3-yl)vinyl)-1H-indol-1-yl)-3-oxopropanoate;
(Z)-2-(5-bromo-1-(2-(dimethylamino)acetyl)-1H-indol-3-yl)-3-(4-methoxypyridin-3-yl)acrylonitrile;
(Z)-2-(4-methylpiperazin-1-yl)ethyl 5-bromo-3-(1-cyano-2-(4-methoxypyridin-3-yl)vinyl)-1H-indole-1-carboxylate;
((Z)-3-(2-(5-bromo-1-(2-(dimethylamino)acetyl)-1H-indol-3-yl)-2-cyanovinyl)-4-methoxybenzonitrile;
(Z)-tert-butyl 5-bromo-3-(1-cyano-2-(5-cyano-2-methoxyphenyl)vinyl)-1H-indole-1-carboxylate;
(R,Z)-benzyl-4-(5-bromo-3-(1-cyano-2-(5-cyano-2-methoxyphenyl)vinyl)-1H-indol-1-yl)-2-(tert-butoxycarbonylamino)-4-oxobutanoate;
(R,Z)-tert-butyl-5-(5-bromo-3-(1-cyano-2-(5-cyano-2-methoxyphenyl)vinyl)-1H-indol-1-yl)-2-(tert-butoxycarbonylamino)-5-oxopentanoate;
(R,Z)-benzyl-2-amino-4-(5-bromo-3-(1-cyano-2-(5-cyano-2-methoxyphenyl)vinyl)-1H-indol-1-yl)-4-oxobutanoate;
(Z)-3-(2-(5-bromo-1-(2-(4-methylpiperazin-1-yl)acetyl)-1H-indol-3-yl)-2-cyanovinyl)-4-methoxybenzonitrile;
(Z)-3-(2-(5-bromo-1-(2-(4-methylpiperazin-1-yl)acetyl)-1H-indol-3-yl)-2-cyanovinyl)-4-methoxybenzonitrile hydrochloride;
(S,Z)-3-(2-(1-(3-aminobutanoyl)-5-bromo-1H-indol-3-yl)-2-cyanovinyl)-4-methoxybenzonitrile hydrochloride;
(Z)-3-(2-(1-(2-aminoacetyl)-5-bromo-1H-indol-3-yl)-2-cyanovinyl)-4-methoxybenzonitrile hydrochloride;
(Z)-3-(2-(5-bromo-1-(2-(piperazin-1-yl)acetyl)-1H-indol-3-yl)-2-cyanovinyl)-4-methoxybenzonitrile hydrochloride;

(Z)-3-(2-(5-bromo-1-(2-(2-(2-methoxyethoxy)ethoxy)acetyl)-1H-indol-3-yl)-2-cyanovinyl)-4-methoxybenzonitrile;
(S,Z)-3-(2-(1-(2-amino-3-hydroxypropanoyl)-5-bromo-1H-indol-3-yl)-2-cyanovinyl)-4-methoxybenzonitrile hydrochloride;
(Z)-3-(2-(5-bromo-1-(5-oxopyrrolidine-2-carbonyl)-1H-indol-3-yl)-2-cyanovinyl)-4-methoxybenzonitrile;
(R,Z)-3-(2-(5-bromo-1-(2,6-diaminohexanoyl)-1H-indol-3-yl)-2-cyanovinyl)-4-methoxybenzonitrile dihydrochloride;
(Z)-3-(5-bromo-3-(1-cyano-2-(5-cyano-2-methoxyphenyl)vinyl)-1H-indol-1-yl)-3-oxopropyl dihydrogen phosphate;
(Z)-2-(1H-indol-3-yl)-3-pyridin-3-yl-acrylonitrile;
(Z)-2-(5-methoxy-1H-indol-3-yl)-3-pyridin-3-yl-acrylonitrile;
(Z)-2-(5-ethoxy-1H-indol-3-yl)-3-pyridin-3-yl-acrylonitrile;
(Z)-2-(5-isopropoxy-1H-indol-3-yl)-3-pyridin-3-yl-acrylonitrile;
(Z)-2-(5-chloro-1H-indol-3-yl)-3-pyridin-3-yl-acrylonitrile;
(Z)-2-(5-fluoro-1H-indol-3-yl)-3-pyridin-3-yl-acrylonitrile;
(Z)-2-(6-methoxy-1H-indol-3-yl)-3-pyridin-3-yl-acrylonitrile;
(Z)-3-(6-fluoropyridin-3-yl)-2-(5-methoxy-1H-indol-3-yl)-acrylonitrile;
(Z)-2-(5-hydroxy-1H-indol-3-yl)-3-pyridin-3-yl-acrylonitrile;
(Z)-3-[2-cyano-2-(5-methoxy-1H-indol-3-yl)-vinyl]-benzonitrile;
(Z)-2-(5-methoxy-1H-indol-3-yl)-3-(4-methyl-pyridin-3-yl)-acrylonitrile;
(Z)-2-(5-bromo-1H-indol-3-yl)-3-pyridin-3-yl-acrylonitrile;
(Z)-2-(5-amino-1H-indol-3-yl)-3-pyridin-3-yl-acrylonitrile;
(Z)-3-(4-chloro-pyridin-3-yl)-2-(5-methoxy-1H-indol-3-yl)-acrylonitrile;
(Z)-3-(6-chloro-pyridin-3-yl)-2-(5-methoxy-1H-indol-3-yl)-acrylonitrile;
(Z)-3-(6-methoxy-pyridin-3-yl)-2-(5-methoxy-1H-indol-3-yl)-acrylonitrile;
(Z)-2-(5-methoxy-1H-indol-3-yl)-3-(6-methyl-pyridin-3-yl)-acrylonitrile;
(Z)-3-[2-cyano-2-(5-hydroxy-1H-indol-3-yl)-vinyl]-benzonitrile;
and their pharmaceutically acceptable salts.
Preferably, the following list of compounds may be cited:
(Z)-2-(5-chloro-1H-indol-3-yl)-3-(4-chloropyridin-3-yl)-acrylonitrile;
(Z)-2-(5-bromo-1H-indol-3-yl)-3-(4-chloropyridin-3-yl)-acrylonitrile;
(Z)-2-(5-bromo-1H-indol-3-yl)-3-(4-methoxypyridin-3-yl)-acrylonitrile;
(E)-2-(5-bromo-1H-indol-3-yl)-3-(4-methoxypyridin-3-yl)-acrylonitrile;
(Z)-2-(5-chloro-1H-indol-3-yl)-3-(4-(dimethylamino)pyridin-3-yl)-acrylonitrile;
(Z)-2-(5-chloro-1H-indol-3-yl)-3-(4-dimethylamino)pyridine-3-yl)-acrylonitrile, hydrochloride;
(Z)-2-(5-bromo-1H-indol-3-yl)-3-(4-(dimethylamino)pyridin-3-yl)-acrylonitrile;
(Z)-2-(5-chloro-1H-indol-3-yl)-3-(4-methoxypyridin-3-yl)-acrylonitrile;
(E)-2-(5-chloro-1H-indol-3-yl)-3-(4-methoxypyridin-3-yl)-acrylonitrile;
(Z)-2-(5-chloro-1H-indol-3-yl)-3-(4-phenoxypyridin-3-yl)-acrylonitrile;
(Z)-2-(5-bromo-1H-indol-3-yl)-3-(4-phenoxypyridin-3-yl)-acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-ethoxypyridin-3-yl)-acrylonitrile;
(Z)-2-(5-bromo-1H-indol-3-yl)-3-(4-isopropoxypyridin-3-yl)-acrylonitrile;
(Z)-2-(5-bromo-1H-indol-3-yl)-3-(4-(methylthio)pyridin-3-yl)-acrylonitrile;
(Z)-2-(5-bromo-1H-indol-3-yl)-3-(4-(ethylthio)pyridin-3-yl)-acrylonitrile;
(Z)-2-(5-bromo-1H-indol-3-yl)-3-(4-(3-bromophenyl)pyridin-3-yl)-acrylonitrile;
(Z)-3-(4-(3-bromophenyl)pyridin-3-yl)-2-(5-chloro-1H-indol-3-yl)-acrylonitrile;
(Z)-2-(5-bromo-1H-indol-3-yl)-3-(4-(phenylthio)pyridin-3-yl)-acrylonitrile;
(Z)-3-(4-(benzylthio)pyridin-3-yl)-2-(5-bromo-1H-indol-3-yl)-acrylonitrile;
(Z)-2-(5-bromo-1H-indol-3-yl)-3-(4-(3,4-dimethoxy)thio)pyridin-3-yl)-acrylonitrile;
(Z)-2-(5-bromo-1H-indol-3-yl)-3-(4-(4-fluorophenoxy)pyridin-3-yl)-acrylonitrile;
(Z)-2-(5-chloro-1H-indol-3-yl)-3-(4-(4-fluorophenoxy)pyridin-3-yl)-acrylonitrile;
(Z)-2-(5-bromo-1H-indol-3-yl)-3-(4-(diethylamino)pyridin-3-yl)-acrylonitrile;
(Z)-2-(5-bromo-1H-indol-3-yl)-3-(4-(4-(trifluoromethyl)phenyl)pyridin-3-yl)-acrylonitrile;
(Z)-2-(5-chloro-1H-indol-3-yl)-3-(4-(4-(trifluoromethyl)phenyl)pyridin-3-yl)-acrylonitrile;
(Z)-2-(5-chloro-1H-indol-3-yl)-3-(4-((4-fluorophenyl)thio)pyridin-3-yl)-acrylonitrile;
(Z)-2-(5-bromo-1H-indol-3-yl)-3-(4-((4-fluorophenyl)thio)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)pyridin-3-yl)-acrylonitrile;
(Z)-2-(5-bromo-1H-indol-3-yl)-3-(4-(pyridine-2-ylthio)pyridin-3-yl)-acrylonitrile;
(Z)-3-(4-(1H-1,2,4-triazol-1-yl)pyridin-3-yl)-2-(5-bromo-1H-indol-3-yl)-acrylonitrile;
(Z)-3-(4-(1H-1,2,4-triazol-1-yl)pyridin-3-yl)-2-(5-chloro-1H-indol-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-2-(5-bromo-1H-indol-3-yl)-3-(4-(2-(dimethylamino)ethylthio)pyridin-3-yl)-acrylonitrile;
(Z)-3-(2-(5-bromo-1H-indol-3-yl)-2-cyanovinyl)-4-(4-fluorophenoxy)benzonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-3-(2-(5-chloro-1H-indol-3-yl)-2-cyanovinyl)-4-methoxybenzonitrile;
(Z)-3-(2-(5-chloro-1H-indol-3-yl)-2-cyanovinyl)-4-(dimethylamino)benzonitrile;

(Z)-3-(2-(5-chloro-1H-indol-3-yl)-2-cyanovinyl)-4-(ethylthio)benzonitrile;
(Z)-N-(3-(2-(5-bromo-1H-indol-3-yl)-2-cyanovinyl)pyridin-4-yl)pivalamide;
(Z)-N-(3-(2-(5-chloro-1H-indol-3-yl)-2-cyanovinyl)pyridin-4-yl)pivalamide;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-2-(5-chloro-1H-indol-3-yl)-3-(4-hydroxypyridin-3-yl)acrylonitrile;
(Z)-3-(2-(5-bromo-1H-indol-3-yl)-2-cyanovinyl)-4-hydroxybenzonitrile;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
(Z)-3-(2-cyano-2-(6-methoxy-1H-indol-3-yl)vinyl)-4-methoxybenzonitrile;
and their pharmaceutically acceptable salts.

More preferably, the following list of compounds may be cited:
(Z)-2-(5-chloro-1H-indol-3-yl)-3-(4-chloropyridin-3-yl)acrylonitrile;
(Z)-2-(5-bromo-1H-indol-3-yl)-3-(4-chloropyridin-3-yl)acrylonitrile;
(Z)-2-(5-bromo-1H-indol-3-yl)-3-(4-methoxypyridin-3-yl)acrylonitrile;
(E)-2-(5-bromo-1H-indol-3-yl)-3-(4-methoxypyridin-3-yl)acrylonitrile;
(Z)-2-(5-chloro-1H-indol-3-yl)-3-(4-methoxypyridin-3-yl)acrylonitrile;
(E)-2-(5-chloro-1H-indol-3-yl)-3-(4-methoxypyridin-3-yl)acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-ethoxypyridin-3-yl)acrylonitrile;
(Z)-2-(5-bromo-1H-indol-3-yl)-3-(4-isopropoxypyridin-3-yl)-acrylonitrile;
(Z)-2-(5-bromo-1H-indol-3-yl)-3-(4-(methylthio)pyridin-3-yl)-acrylonitrile;
(Z)-2-(5-bromo-1H-indol-3-yl)-3-(4-(phenylthio)pyridin-3-yl)-acrylonitrile;
(Z)-3-(4-(benzylthio)pyridin-3-yl)-2-(5-bromo-1H-indol-3-yl)-acrylonitrile;
(Z)-2-(5-bromo-1H-indol-3-yl)-3-(4-(4-fluorophenoxy)pyridin-3-yl)-acrylonitrile;
(Z)-2-(5-chloro-1H-indol-3-yl)-3-(4-(4-fluorophenoxy)pyridin-3-yl)-acrylonitrile;
(Z)-2-(5-bromo-1H-indol-3-yl)-3-(4-(dimethylamino)pyridin-3-yl)-acrylonitrile;
(Z)-2-(5-bromo-1H-indol-3-yl)-3-(4-(diethylamino)pyridin-3-yl)-acrylonitrile;
(Z)-2-(5-bromo-1H-indol-3-yl)-3-(4-(4-(trifluoromethyl)phenyl)pyridin-3-yl)-acrylonitrile;
(Z)-2-(5-chloro-1H-indol-3-yl)-3-(4-((4-fluorophenyl)thio)pyridin-3-yl)-acrylonitrile;
(Z)-2-(5-bromo-1H-indol-3-yl)-3-(4-((4-fluorophenyl)thio)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)pyridin-3-yl)-acrylonitrile;
(Z)-3-(4-(1H-1,2,4-triazol-1-yl)pyridin-3-yl)-2-(5-bromo-1H-indol-3-yl)-acrylonitrile;
(Z)-3-(4-(1H-1,2,4-triazol-1-yl)pyridin-3-yl)-2-(5-chloro-1H-indol-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
and their pharmaceutically acceptable salts.

More preferably, the following list of compounds may be cited:
(Z)-2-(5-chloro-1H-indol-3-yl)-3-(4-chloropyridin-3-yl)-acrylonitrile;
(Z)-2-(5-bromo-1H-indol-3-yl)-3-(4-chloropyridin-3-yl)-acrylonitrile;
(Z)-2-(5-bromo-1H-indol-3-yl)-3-(4-methoxypyridin-3-yl)-acrylonitrile;
(E)-2-(5-bromo-1H-indol-3-yl)-3-(4-methoxypyridin-3-yl)-acrylonitrile;
(Z)-2-(5-chloro-1H-indol-3-yl)-3-(4-methoxypyridin-3-yl)-acrylonitrile;
(E)-2-(5-chloro-1H-indol-3-yl)-3-(4-methoxypyridin-3-yl)-acrylonitrile;
(Z)-2-(5-bromo-1H-indol-3-yl)-3-(4-(dimethylamino)pyridin-3-yl)-acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-(methylthio)pyridin-3-yl)-acrylonitrile;
(Z)-2-(5-bromo-1H-indol-3-yl)-3-(4-(diethylamino)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;

(Z)-3-(2-(5-bromo-1H-indol-3-yl)-2-cyanovinyl)-4-(dimethylamino)benzonitrile;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
and their pharmaceutically acceptable salts.

In another embodiment, compounds are chosen from the group consisting of:
(Z)-2-(1-acetyl-5-bromo-1H-indol-3-yl)-3-(4-methoxypyridin-3-yl)acrylonitrile;
(Z)-3-(2-(1-acetyl-5-bromo-1H-indol-3-yl)-2-cyanovinyl)-4-methoxybenzonitrile;
(Z)-2-(5-bromo-1-pivaloyl-1H-indol-3-yl)-3-(4-methoxypyridin-3-yl)acrylonitrile;
(Z)-3-(2-(5-bromo-1-pivaloyl-1H-indol-3-yl)-2-cyanovinyl)-4-methoxybenzonitrile;
(Z)-methyl 3-(5-bromo-3-(1-cyano-2-(4-methoxypyridin-3-yl)vinyl)-1H-indol-1-yl)-3-oxopropanoate;
(Z)-2-(5-bromo-1-(2-(dimethylamino)acetyl)-1H-indol-3-yl)-3-(4-methoxypyridin-3-yl)acrylonitrile;
(Z)-2-(4-methylpiperazin-1-yl)ethyl 5-bromo-3-(1-cyano-2-(4-methoxypyridin-3-yl)vinyl)-1H-indole-1-carboxylate;
((Z)-3-(2-(5-bromo-1-(2-(dimethylamino)acetyl)-1H-indol-3-yl)-2-cyanovinyl)-4-methoxybenzonitrile;
(Z)-tert-butyl 5-bromo-3-(1-cyano-2-(5-cyano-2-methoxyphenyl)vinyl)-1H-indole-1-carboxylate;
(R,Z)-benzyl-4-(5-bromo-3-(1-cyano-2-(5-cyano-2-methoxyphenyl)vinyl)-1H-indol-1-yl)-2-(tert-butoxycarbonylamino)-4-oxobutanoate;
(R,Z)-tert-butyl-5-(5-bromo-3-(1-cyano-2-(5-cyano-2-methoxyphenyl)vinyl)-1H-indol-1-yl)-2-(tert-butoxycarbonylamino)-5-oxopentanoate;
(R,Z)-benzyl-2-amino-4-(5-bromo-3-(1-cyano-2-(5-cyano-2-methoxyphenyl)vinyl)-1H-indol-1-yl)-4-oxobutanoate;
(Z)-3-(2-(5-bromo-1-(2-(4-methylpiperazin-1-yl)acetyl)-1H-indol-3-yl)-2-cyanovinyl)-4-methoxybenzonitrile;
(Z)-3-(2-(5-bromo-1-(2-(4-methylpiperazin-1-yl)acetyl)-1H-indol-3-yl)-2-cyanovinyl)-4-methoxybenzonitrile hydrochloride;
(S,Z)-3-(2-(1-(3-aminobutanoyl)-5-bromo-1H-indol-3-yl)-2-cyanovinyl)-4-methoxybenzonitrile hydrochloride;
(Z)-3-(2-(1-(2-aminoacetyl)-5-bromo-1H-indol-3-yl)-2-cyanovinyl)-4-methoxybenzonitrile hydrochloride;
(Z)-3-(2-(5-bromo-1-(2-(piperazin-1-yl)acetyl)-1H-indol-3-yl)-2-cyanovinyl)-4-methoxybenzonitrile hydrochloride;
(Z)-3-(2-(5-bromo-1-(2-(2-(2-methoxyethoxy)ethoxy)acetyl)-1H-indol-3-yl)-2-cyanovinyl)-4-methoxybenzonitrile;
(S,Z)-3-(2-(1-(2-amino-3-hydroxypropanoyl)-5-bromo-1H-indol-3-yl)-2-cyanovinyl)-4-methoxybenzonitrile hydrochloride;
(Z)-3-(2-(5-bromo-1-(5-oxopyrrolidine-2-carbonyl)-1H-indol-3-yl)-2-cyanovinyl)-4-methoxybenzonitrile;
(R,Z)-3-(2-(5-bromo-1-(2,6-diaminohexanoyl)-1H-indol-3-yl)-2-cyanovinyl)-4-methoxybenzonitrile dihydrochloride;
(Z)-3-(5-bromo-3-(1-cyano-2-(5-cyano-2-methoxyphenyl)vinyl)-1H-indol-1-yl)-3-oxopropyl dihydrogen phosphate;
and their pharmaceutically acceptable salts.

Preferably, compounds are chosen from the group consisting of:
(Z)-2-(1-acetyl-5-bromo-1H-indol-3-yl)-3-(4-methoxypyridin-3-yl)acrylonitrile;
(Z)-3-(2-(1-acetyl-5-bromo-1H-indol-3-yl)-2-cyanovinyl)-4-methoxybenzonitrile;
(Z)-2-(5-bromo-1-pivaloyl-1H-indol-3-yl)-3-(4-methoxypyridin-3-yl)acrylonitrile;
(Z)-3-(2-(5-bromo-1-pivaloyl-1H-indol-3-yl)-2-cyanovinyl)-4-methoxybenzonitrile;
(Z)-methyl 3-(5-bromo-3-(1-cyano-2-(4-methoxypyridin-3-yl)vinyl)-1H-indol-1-yl)-3-oxopropanoate;
(Z)-2-(5-bromo-1-(2-(dimethylamino)acetyl)-1H-indol-3-yl)-3-(4-methoxypyridin-3-yl)acrylonitrile;
(Z)-2-(4-methylpiperazin-1-yl)ethyl 5-bromo-3-(1-cyano-2-(4-methoxypyridin-3-yl)vinyl)-1H-indole-1-carboxylate;
((Z)-3-(2-(5-bromo-1-(2-(dimethylamino)acetyl)-1H-indol-3-yl)-2-cyanovinyl)-4-methoxybenzonitrile;
(Z)-tert-butyl 5-bromo-3-(1-cyano-2-(5-cyano-2-methoxyphenyl)vinyl)-1H-indole-1-carboxylate;
(R,Z)-benzyl-4-(5-bromo-3-(1-cyano-2-(5-cyano-2-methoxyphenyl)vinyl)-1H-indol-1-yl)-2-(tert-butoxycarbonylamino)-4-oxobutanoate;
(R,Z)-tert-butyl-5-(5-bromo-3-(1-cyano-2-(5-cyano-2-methoxyphenyl)vinyl)-1H-indol-1-yl)-2-(tert-butoxycarbonylamino)-5-oxopentanoate;
(R,Z)-benzyl-2-amino-4-(5-bromo-3-(1-cyano-2-(5-cyano-2-methoxyphenyl)vinyl)-1H-indol-1-yl)-4-oxobutanoate;
(R,Z)-3-(2-(5-bromo-1-(2,6-diaminohexanoyl)-1H-indol-3-yl)-2-cyanovinyl)-4-methoxybenzonitrile dihydrochloride;
(Z)-3-(5-bromo-3-(1-cyano-2-(5-cyano-2-methoxyphenyl)vinyl)-1H-indol-1-yl)-3-oxopropyl dihydrogen phosphate;
and their pharmaceutically acceptable salts.

In a more preferred embodiment, compounds are chosen from the group consisting of:
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
and their pharmaceutically acceptable salts. A preferred compound is (Z)-3-(2-(5-bromo-1H-indol-3-yl)-2-cyanovinyl)-4-methoxybenzonitrile having the following formula:

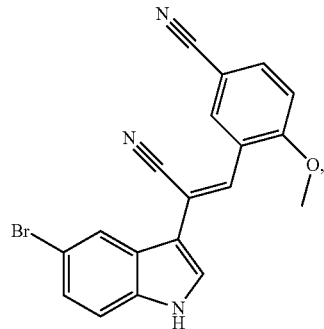

and also named compound "38" herein.

The chemical structures of compounds of the invention and the methods of preparation thereof are disclosed in WO 2010/150211 and WO 2014/086964.

The present invention relates to:

- a pharmaceutical composition comprising any compound having the formula (I), (Ia), (Ib) or (II) as defined above including anyone of the disclosed embodiments for use for treating and/or preventing endometriosis; and/or
- a pharmaceutical composition comprising any compound having the formula (I), (Ia), (Ib) or (II) as defined above including anyone of the disclosed embodiments, and a pharmaceutically acceptable carrier for use for treating and/or preventing endometriosis; and/or
- a pharmaceutical composition comprising (a) any compound having the formula (I), (Ia), (Ib) or (II) as defined above including anyone of the disclosed embodiments, and (b) an additional anti-endometriosis drug for use for treating and/or preventing endometriosis; and/or
- a product or kit containing (a) any compound of formula (I), (Ia), (Ib) or (II) as disclosed above including anyone of the disclosed embodiments and (b) an additional anti-endometriosis drug, as a combined preparation for simultaneous, separate or sequential use, in the treatment of endometriosis; and/or
- a combined preparation which comprises (a) any compound of formula (I), (Ia), (Ib) or (II) as disclosed above including anyone of the disclosed embodiments and (b) an additional anti-endometriosis drug, for simultaneous, separate or sequential use in the treatment of endometriosis; and/or
- the use of a pharmaceutical composition as defined above or any compound having the formula (I), (Ia), (Ib) or (II) as defined above including anyone of the disclosed embodiments, for the manufacture of a medicament for the treatment of endometriosis; and/or
- the use of a pharmaceutical composition as defined above or any compound having the formula (I), (Ia), (Ib) or (II) as defined above including anyone of the disclosed embodiments and (b) an additional anti-endometriosis drug, for the manufacture of a medicament for the treatment of endometriosis; and/or
- a method for treating endometriosis in a subject in need thereof, comprising administering an effective amount of a pharmaceutical composition as defined above or any compound having the formula (I), (Ia), (Ib) or (II) as defined above including anyone of the disclosed embodiments; and/or
- a method for treating endometriosis in a subject in need thereof, comprising administering an effective amount of a pharmaceutical composition as defined above or any compound having the formula (I), (Ia), (Ib) or (II) as defined above including anyone of the disclosed embodiments and a pharmaceutically acceptable carrier; and/or
- a method for treating endometriosis in a subject in need thereof, comprising administering an effective amount of a pharmaceutical composition as defined above or any compound having the formula (I), (Ia), (Ib) or (II) as defined above including anyone of the disclosed embodiments, and (b) an additional anti-endometriosis drug; and/or
- a method for treating endometriosis in a subject in need thereof, comprising administering an effective amount of a pharmaceutical composition as defined above or any compound having the formula (I), (Ia), (Ib) or (II) as defined above including anyone of the disclosed embodiments, and an effective amount of a pharmaceutical composition comprising an anti-endometriosis drug.

As used herein, the term "treatment", "treat" or "treating" refers to any act intended to ameliorate the health status of patients such as therapy, prevention, prophylaxis and retardation of endometriosis. In certain embodiments, such term refers to the amelioration or eradication of a disease or symptoms associated with endometriosis. In other embodiments, this term refers to minimizing the spread or worsening of endometriosis resulting from the administration of one or more therapeutic agents to a subject with such a disease.

By "effective amount" it is meant the quantity of the pharmaceutical composition of the invention which prevents, removes or reduces the deleterious effects of endometriosis in mammals, including humans. It is understood that the administered dose may be adapted by those skilled in the art according to the patient, the pathology, the mode of administration, etc. For instance, the compounds of the invention may be used at a dose of 0.01 to 500, 1 to 300, 5 to 150, 10 to 100, preferably about 40 or 100 mg/kg of body weight. In a particular embodiment, the pharmaceutical compositions according to the invention comprise from 0.01 to 500, 1 to 300, 5 to 150, 10 to 100, preferably about 40 or 100 mg/kg of bodyweight of the compound of the invention. The compositions of the invention can be administered once a day, every two days, twice per week, once a week, twice a month, once a month . . . . It is understood that the administered dose may be adapted by those skilled in the art according to the patient, the pathology, the mode of administration, etc. In a preferred embodiment, a composition of the invention comprises a compound as defined herein at a dose of 40 mg/kg of bodyweight. Such preferred composition can be administered in a human once a day, every two days, twice per week, once a week, twice a month, once a month, preferably once a day.

As used herein, the terms "subject" or "patient" refer to any subject or patient who may suffer from endometriosis. Preferably, such terms include mammals, preferably humans, and more preferably women. In a particular embodiment, the "subject" or "patient" does not suffer from cancer or has no cancer, such as an ovarian or a breast cancer.

As used herein, the term "about" will be understood by a person of ordinary skill in the art and will vary to some extent on the context in which it is used. If there are uses of the term which are not clear to persons of ordinary skill in the art given the context in which it is used, "about" will mean up to plus or minus 20%, preferably 10% of the particular term.

The administration route can be topical, transdermal, oral, rectal, sublingual, intranasal, intrathecal, intratumoral or parenteral (including subcutaneous, intramuscular, intravenous and/or intradermal). Preferably, the administration route is parental, preferably by intravenous injection. The pharmaceutical composition is adapted for one or several of the above-mentioned routes. The pharmaceutical composition, kit, product or combined preparation is preferably administered by injection or by intravenous infusion or suitable sterile solutions, or in the form of liquid or solid doses via the alimentary canal.

The pharmaceutical composition can be formulated as solutions in pharmaceutically compatible solvents or as emulsions, suspensions or dispersions in suitable pharmaceutical solvents or vehicles, or as pills, tablets or capsules that contain solid vehicles in a way known in the art.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. Formulations for rectal administration may be in the form of a suppository incorporating the active ingredient and carrier such as cocoa butter, or in the form of an enema. Formulations suitable for parenteral administration conveniently comprise a sterile oily or aqueous preparation of the active ingredient which is preferably isotonic with the blood of the recipient. Every such formulation can also contain other pharmaceutically compatible and nontoxic auxiliary agents, such as, e.g. stabilizers, antioxidants, binders, dyes, emulsifiers or flavouring substances. The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions or as oral dosage by the digestive tract. More advantageously, the pharmaceutical compositions are applied by intravenous injection of nanosuspensions, preferably comprising between 1 and 100 mg/mL, more preferably about 50 mg/mL of a compound as defined herein. Methods for the safe and effective administration of most of these chemotherapeutic agents are known to those skilled in the art. In addition, their administration is described in the standard literature.

The additional anti-endometriosis drug can be selected in the non-exhaustive list of anti-endometriosis agents. By "anti-endometriosis drug", it means any agent having a therapeutic effect for preventing and/or treating endometriosis. Particularly, the anti-endometriosis drug is selected in the group consisting of nonsteroidal anti-inflammatory drugs (NSAIDs), opioids, hormonal contraceptives drugs, growth factor inhibitors, endogenous angiogenesis inhibitors, fumagillin analogues, statins, cyclo-oxygenase-2 inhibitors, phytochemical compounds, immunomodulators, dopamine agonists, peroxisome proliferator-activated receptor agonists, progestins, danazol, and gonadotropin-releasing hormone agonists.

Further aspects and advantages of the invention will be disclosed in the following experimental section. The examples below illustrate the present invention and are given as non-limiting illustrations

FIGURES

Figure 2:
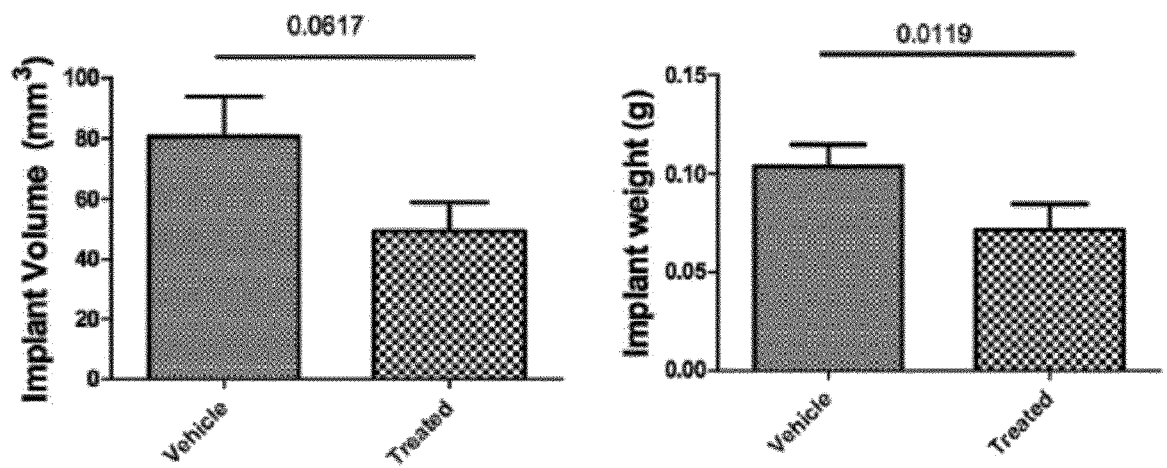

FIG. 1: Protocol phase of the experimental study.
FIG. 2: Ex vivo clinical evaluation (implant volume (mm$^3$) and weight (g)) in syngenic mice.

EXAMPLES

Example 1: Echographic and Ex Vivo Evaluation of Endometriosis Lesions in Syngenic Mice Treated with Compound 38

Protocol:
The protocol is summarized in FIG. 1. More particularly, 20 syngenic mices were engraved estradiol at D-1. Intraperitoneal Uterine Horsn implant have been implanted in each mouse at D0. A nanosuspension of compound 38 (50 mg/mL) has been intravenously administered in 10 mice (treated group) at a 100 mg/kg/BW dose from D7 to D21 every 2 days.

Mices have been sacrified at D23 and implants have been removed for ex vivo clinical evaluation.

Results:
As shown by FIG. 2 illustrating ex vivo clinical evaluation, both implant volume and weight for treated mice are lower than those of the control group (Vehicle).

Such results prove the therapeutic effect of reducing endometriosis lesions for the compounds of the invention, thereby demonstrating an efficient effect for treating and/or preventing endometriosis.

The invention claimed is:
1. A method for treating endometriosis in a subject in need thereof, comprising administering an effective amount of a compound of formula (I):

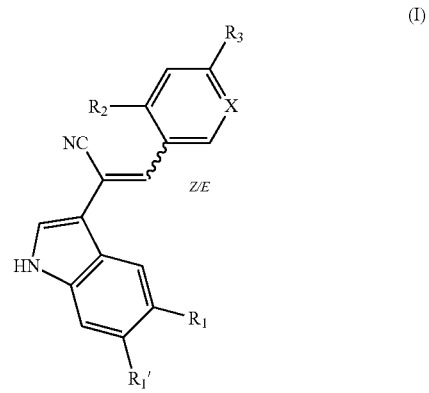

wherein:
X represents a nitrogen atom, a C—CN unit or a N+—O— unit;
$R_1$ and $R_1'$ represent independently H, a halogen, a hydroxy, an amino, or a ($C_1$-$C_6$)alkoxy group, optionally substituted by a carboxylic group or one —$NR_{11}R_{12}$ unit wherein $R_{11}$ and $R_{12}$ represent H, a ($C_1$-$C_6$)alkyl group, or $R_{11}$ and $R_{12}$ taken together form a 3- to 7-membered ring, optionally interrupted by one or several heteroatoms;
$R_2$ represents:
a radical ($C_1$-$C_3$)alkyl, ($C_1$-$C_6$)alkoxy, ($C_3$-$C_6$)cycloalkoxy, aryloxy, heteroaryloxy, ($C_1$-$C_6$)alkyl-aryloxy, ($C_1$-$C_6$)alkyl-heteroaryloxy, said radicals being optionally substituted by at least one halogen, or a radical thio-($C_1$-$C_6$)alkyl, thio-aryl, thio-heteroaryl, thio-($C_1$-$C_6$)alkyl-aryl or thio-($C_1$-$C_6$)-alkyl-heteroaryl, said radicals being optionally substituted by at least one halogen or by a ($C_1$-$C_6$)alkoxy group,
a —$NR_4R_5$ unit, a O—($C_1$-$C_6$)alkyl-$NR_4R_5$ unit or a S—($C_1$-$C_6$)alkyl-$NR_4R_5$ unit wherein $R_4$ and $R_5$ represent H, a ($C_1$-$C_6$)alkyl group, or $R_4$ and $R_5$ taken together form a 3- to 7-membered ring, optionally interrupted by one or several heteroatoms, with the proviso that at least one among $R_4$ and $R_5$ is not H,
a $NHCOR_6$ unit wherein $R_6$ represents ($C_1$-$C_6$)alkyl group,
an aryl or heteroaryl group optionally substituted by at least one halogen, a trifluoromethyl group, or a ($C_1$-$C_3$)alkoxy group, a halogen, or
a hydroxy; and
R$_3$ represents a hydrogen, a (C$_1$-C$_3$)alkyl group, a (C$_1$-C$_3$)alkoxy group or a halogen; and the compounds of formula (I) as above defined, in which the nitrogen atom of the indole core is substituted by a group selected from the group consisting of a COR$_7$ and a CO$_2$R$_7$ group, wherein R$_7$ represents:
   a (C$_1$-C$_6$)alkyl group, optionally substituted by at least a hydroxy group, a (C$_1$-C$_6$)alkyloxy group, a (C$_1$-C$_6$)$_n$polyalkyloxy group wherein n is 1<n<6, a phosphate or pyrophosphate group and salts or (C$_1$-C$_3$) alkyl ester thereof, a R$_8$ group, a —NHCO$_2$R$_8$ unit, a COR$_8$ group, or a CO$_2$R$_8$ group, wherein R$_8$ is:
   a (C$_1$-C$_6$)alkyl group;
   an aryl, a (C$_1$-C$_6$)alkylaryl, or a heteroaryl;
   a —NR$_9$R$_{10}$ unit wherein R$_9$ and R$_{10}$ represent a hydrogen, a (C$_1$-C$_6$)alkyl group, or R$_9$ and R$_{10}$ taken together form a 3- to 7-membered ring, optionally interrupted by one or several heteroatoms, and optionally the ring being substituted by at least one (C$_1$-C$_6$)alkyl group;
   a NH—NR$_9$R$_{10}$ unit wherein R$_9$ and R$_{10}$ are as defined above; or
   a saturated heterocycle or a heteroaryl;
or one of its pharmaceutically acceptable salts.

2. The method according to claim 1, wherein the compound has the formula (Ia):

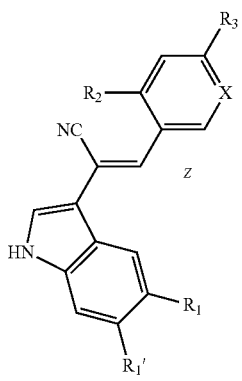

(Ia)

wherein X, R$_1$, R$_1$', R$_2$, and R$_3$ are as defined in claim 1.

3. The method according to claim 1, wherein the compound has the formula (Ib):

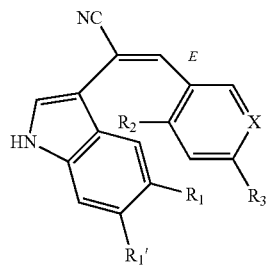

(Ib)

wherein X, R, R$_1$', R$_2$, and R$_3$ are as defined in claim 1.

4. The method according to claim 1, wherein R$_1$' is H.

5. The method according to claim 1, wherein R$_1$ represents a halogen selected from the group consisting of a bromine and a chlorine.

6. The method according to claim 1, wherein R$_1$ is H.

7. The method according to claim 1, wherein R$_1$' is a halogen selected from a bromine, a chlorine, or a fluorine.

8. The method according to claim 1, wherein R$_2$ represents:
   a radical (C$_1$-C$_6$)alkoxy, or phenoxy, said radicals being optionally substituted by at least one halogen;
   a halogen;
   a R$_4$—N—R$_5$ unit or a S—(C$_1$-C$_6$)alkyl-NR$_4$R$_5$ unit, wherein R$_4$ and R$_5$ represent H or a (C$_1$-C$_6$)alkyl group, with the proviso that at least one among R$_4$ and R$_5$ is not H;
   a NHCOR$_6$ unit wherein R$_6$ represents (C$_1$-C$_6$)alkyl group;
   a radical thio-(C$_1$-C$_6$)alkyl, thio-aryl, thio-heteroaryl, thio-(C$_1$-C$_6$)alkyl-aryl, said radicals being optionally substituted by at least one halogen or by a (C$_1$-C$_6$) alkoxy group;
   an aryl group optionally substituted by at least one halogen, or a trifluoromethyl group; or
   a heteroaryl group.

9. The method according to claim 1, wherein R$_2$ represents:
   a radical (C$_1$-C$_6$)alkoxy selected from the group consisting of a methoxy group, an ethoxy group, and an isopropoxy group, or a phenoxy group, optionally substituted by a fluorine;
   a halogen selected from the group consisting of a fluorine and a chlorine;
   a R$_4$—N—R$_5$ unit or a S—(C$_1$-C$_6$)alkyl-NR$_4$R$_5$ unit wherein R$_4$ and R$_5$ represent a methyl or an ethyl group;
   a NHCOR$_6$ unit wherein R$_6$ represents a tert-butyl group;
   a radical selected in the group consisting of a thio-methyl group, a thio-ethyl group, a thio-benzyl group, a thio-pyridinyl group and a thio-phenyl group, optionally substituted by at least one fluorine or a trifluoromethyl group;
   a phenyl group optionally substituted by at least one bromine or a trifluoromethyl group; or
   a heteroaryl group selected from the group consisting of a furan or a triazol.

10. The method according to claim 1, wherein said compound is selected from the group consisting of:
   (Z)-3-(4-ethoxypyridin-3-yl)-2-(5-methoxy-1H-indol-3-yl)-acrylonitrile;
   (Z)-2-(5-chloro-1H-indol-3-yl)-3-(4-chloropyridin-3-yl)-acrylonitrile;
   (Z)-2-(5-bromo-1H-indol-3-yl)-3-(4-chloropyridin-3-yl)-acrylonitrile;
   (Z)-2-(5-bromo-1H-indol-3-yl)-3-(4-methoxypyridin-3-yl)-acrylonitrile;
   (E)-2-(5-bromo-1H-indol-3-yl)-3-(4-methoxypyridin-3-yl)-acrylonitrile;
   (Z)-2-(5-chloro-1H-indol-3-yl)-3-(4-(dimethylamino) pyridin-3-yl)-acrylonitrile;
   (Z)-2-(5-chloro-1H-indol-3-yl)-3-(4-dimethylamino) pyridine-3-yl)-acrylonitile hydrochloride;
   (Z)-2-(5-bromo-1H-indol-3-yl)-3-(4-(dimethylamino) pyridin-3-yl)-acrylonitrile;
   (Z)-2-(5-chloro-1H-indol-3-yl)-3-(4-methoxypyridin-3-yl)-acrylonitrile;
   (E)-2-(5-chloro-1H-indol-3-yl)-3-(4-methoxypyridin-3-yl)-acrylonitrile;
   (Z)-2-(5-chloro-1H-indol-3-yl)-3-(4-phenoxypyridin-3-yl)-acrylonitrile;
   (Z)-2-(5-bromo-1H-indol-3-yl)-3-(4-phenoxypyridin-3-yl)-acrylonitrile;

(Z)-2-(5-methoxy-1H-indol-3-yl)-3-(4-methoxypyridin-3-yl)-acrylonitrile;
(Z)-2-(5-bromo-1H-indol-3-yl)-3-(4-ethoxypyridin-3-yl)-acrylonitile;
(Z)-2-(5-bromo-1H-indol-3-yl)-3-(4-isopropoxypyridin-3-yl)-acrylonitile;
(Z)-2-(5-bromo-1H-indol-3-yl)-3-(4-(methylthio)pyridin-3-yl)-acrylonitrile;
(Z)-2-(5-bromo-1H-indol-3-yl)-3-(4-(ethylthio)pyridin-3-yl)-acrylonitrile;
(Z)-2-(5-bromo-1H-indol-3-yl)-3-(4-(3-bromophenyl)pyridin-3-yl)-acrylonitrile;
(Z)-3-(4-(3-bromophenyl)pyridin-3-yl)-2-(5-chloro-1H-indol-3-yl)-acrylonitrile;
(Z)-2-(5-bromo-1H-indol-3-yl)-3-(4-(phenylthio)pyridin-3-yl)-acrylonitile;
(Z)-3-(4-(benzylthio)pyridin-3-yl)-2-(5-bromo-1H-indol-3-yl)-acrylonitrile;
(Z)-2-(5-bromo-1H-indol-3-yl)-3-(4-(3,4-dimethoxy)thio)pyridin-3-yl)-acrylonitrile;
(Z)-2-(5-bromo-1H-indol-3-yl)-3-(4-(4-fluorophenoxy)pyridin-3-yl)-acrylonitrile;
(Z)-2-(5-chloro-1H-indol-3-yl)-3-(4-(4-fluorophenoxy)pyridin-3-yl)-acrylonitrile;
(Z)-2-(5-bromo-1H-indol-3-yl)-3-(4-(diethylamino)pyridin-3-yl)-acrylonitrile;
(Z)-2-(5-bromo-1H-indol-3-yl)-3-(4-(4-(trifluoromethyl)phenyl)pyridin-3-yl)-acrylonitrile;
(Z)-2-(5-chloro-1H-indol-3-yl)-3-(4-(4-(trifluoromethyl)phenyl)pyridin-3-yl)-acrylonitrile;
(Z)-2-(5-chloro-1H-indol-3-yl)-3-(4-((4-fluorophenyl)thio)pyridin-3-yl)-acrylonitrile;
(Z)-2-(5-bromo-1H-indol-3-yl)-3-(4-((4-fluorophenyl)thio)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)pyridin-3-yl)-acrylonitrile;
(Z)-2-(5-bromo-1H-indol-3-yl)-3-(4-(pyridine-2-ylthio)pyridin-3-yl)-acrylonitrile;
(Z)-3-(4-(1H-1,2,4-triazol-1-yl)pyridin-3-yl)-2-(5-bromo-1H-indol-3-yl)-acrylonitile;
(Z)-3-(4-(1H-1,2,4-triazol-1-yl)pyridin-3-yl)-2-(5-chloro-1H-indol-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-2-(5-bromo-1H-indol-3-yl)-3-(4-(2-(dimethylamino)ethylthio)pyridin-3-yl)-acrylonitrile;
(Z)-3-(2-(5-bromo-1H-indol-3-yl)-2-cyanovinyl)-4-(4-fluorophenoxy)benzonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-3-(2-(5-chloro-1H-indol-3-yl)-2-cyanovinyl)-4-methoxybenzonitrile;
(Z)-3-(2-(5-chloro-1H-indol-3-yl)-2-cyanovinyl)-4-(dimethylamino)benzonitrile;
(Z)-3-(2-(5-chloro-1H-indol-3-yl)-2-cyanovinyl)-4-(ethylthio)benzonitrile;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
(Z)-3-(2-cyano-2-(6-methoxy-1H-indol-3-yl)vinyl)-4-methoxybenzonitrile;
(Z)-2-(1-acetyl-5-bromo-1H-indol-3-yl)-3-(4-methoxypyridin-3-yl)acrylonitrile;
(Z)-3-(2-(1-acetyl-5-bromo-1H-indol-3-yl)-2-cyanovinyl)-4-methoxybenzonitrile;
(Z)-2-(5-bromo-1-pivaloyl-1H-indol-3-yl)-3-(4-methoxypyridin-3-yl)acrylonitrile;
(Z)-3-(2-(5-bromo-1-pivaloyl-1H-indol-3-yl)-2-cyanovinyl)-4-methoxybenzonitrile;
(Z)-methyl 3-(5-bromo-3-(1-cyano-2-(4-methoxypyridin-3-yl)vinyl)-1H-indol-1-yl)-3-oxopropanoate;
(Z)-2-(5-bromo-1-(2-(dimethylamino)acetyl)-1H-indol-3-yl)-3-(4-methoxypyridin-3-yl)acrylonitrile;
(Z)-2-(4-methylpiperazin-1-yl)ethyl 5-bromo-3-(1-cyano-2-(4-methoxypyridin-3-yl)vinyl)-1H-indole-1-carboxylate;
((Z)-3-(2-(5-bromo-1-(2-(dimethylamino)acetyl)-1H-indol-3-yl)-2-cyanovinyl)-4-methoxybenzonitrile;
(Z)-tert-butyl 5-bromo-3-(1-cyano-2-(5-cyano-2-methoxyphenyl)vinyl)-1H-indole-1-carboxylate;
(R,Z)-benzyl-4-(5-bromo-3-(1-cyano-2-(5-cyano-2-methoxyphenyl)vinyl)-1H-indol-1-yl)-2-(tert-butoxycarbonylamino)-4-oxobutanoate;
(R,Z)-tert-butyl-5-(5-bromo-3-(1-cyano-2-(5-cyano-2-methoxyphenyl)vinyl)-1H-indol-1-yl)-2-(tert-butoxycarbonylamino)-5-oxopentanoate;
(R,Z)-benzyl-2-amino-4-(5-bromo-3-(1-cyano-2-(5-cyano-2-methoxyphenyl)vinyl)-1H-indol-1-yl)-4-oxobutanoate;
(Z)-3-(2-(5-bromo-1-(2-(4-methylpiperazin-1-yl)acetyl)-1H-indol-3-yl)-2-cyanovinyl)-4-methoxybenzonitrile;
(Z)-3-(2-(5-bromo-1-(2-(4-methylpiperazin-1-yl)acetyl)-1H-indol-3-yl)-2-cyanovinyl)-4-methoxybenzonitrile hydrochloride;
(S,Z)-3-(2-(1-(3-aminobutanoyl)-5-bromo-1H-indol-3-yl)-2-cyanovinyl)-4-methoxybenzonitrile hydrochloride;
(Z)-3-(2-(1-(2-aminoacetyl)-5-bromo-1H-indol-3-yl)-2-cyanovinyl)-4-methoxybenzonitrile hydrochloride;
(Z)-3-(2-(5-bromo-1-(2-(piperazin-1-yl)acetyl)-1H-indol-3-yl)-2-cyanovinyl)-4-methoxybenzonitrile hydrochloride;
(Z)-3-(2-(5-bromo-1-(2-(2-(2-methoxyethoxy)ethoxy)acetyl)-1H-indol-3-yl)-2-cyanovinyl)-4-methoxybenzonitrile;

(S,Z)-3-(2-(1-(2-amino-3-hydroxypropanoyl)-5-bromo-1H-indol-3-yl)-2-cyanovinyl)-4-methoxybenzonitrile hydrochloride;

(Z)-3-(2-(5-bromo-1-(5-oxopyrrolidine-2-carbonyl)-1H-indol-3-yl)-2-cyanovinyl)-4-methoxybenzonitrile;

(R,Z)-3-(2-(5-bromo-1-(2,6-diaminohexanoyl)-1H-indol-3-yl)-2-cyanovinyl)-4-methoxybenzonitrile dihydrochloride;

(Z)-3-(5-bromo-3-(1-cyano-2-(5-cyano-2-methoxyphenyl)vinyl)-1H-indol-1-yl)-3-oxopropyl dihydrogen phosphate;

(Z)-2-(1H-indol-3-yl)-3-pyridin-3-yl-acrylonitrile;

(Z)-2-(5-methoxy-1H-indol-3-yl)-3-pyridin-3-yl-acrylonitrile;

(Z)-2-(5-ethoxy-1H-indol-3-yl)-3-pyridin-3-yl-acrylonitrile;

(Z)-2-(5-isopropoxy-1H-indol-3-yl)-3-pyridin-3-yl-acrylonitrile;

(Z)-2-(5-chloro-1H-indol-3-yl)-3-pyridin-3-yl-acrylonitrile;

(Z)-2-(5-fluoro-1H-indol-3-yl)-3-pyridin-3-yl-acrylonitrile;

(Z)-2-(6-methoxy-1H-indol-3-yl)-3-pyridin-3-yl-acrylonitrile;

(Z)-3-(6-fluoropyridin-3-yl)-2-(5-methoxy-1H-indol-3-yl)-acrylonitrile;

(Z)-2-(5-hydroxy-1H-indol-3-yl)-3-pyridin-3-yl-acrylonitrile;

(Z)-3-[2-cyano-2-(5-methoxy-1H-indol-3-yl)-vinyl]-benzonitrile;

(Z)-2-(5-methoxy-1H-indol-3-yl)-3-(4-methyl-pyridin-3-yl)-acrylonitrile;

(Z)-2-(5-bromo-1H-indol-3-yl)-3-pyridin-3-yl-acrylonitrile;

(Z)-2-(5-amino-1H-indol-3-yl)-3-pyridin-3-yl-acrylonitrile;

(Z)-3-(4-chloro-pyridin-3-yl)-2-(5-methoxy-1H-indol-3-yl)-acrylonitrile;

(Z)-3-(6-chloro-pyridin-3-yl)-2-(5-methoxy-1H-indol-3-yl)-acrylonitrile;

(Z)-3-(6-methoxy-pyridin-3-yl)-2-(5-methoxy-1H-indol-3-yl)-acrylonitrile;

(Z)-2-(5-methoxy-1H-indol-3-yl)-3-(6-methyl-pyridin-3-yl)-acrylonitrile; and (Z)-3-[2-cyano-2-(5-hydroxy-1H-indol-3-yl)-vinyl]-benzonitrile;

and their pharmaceutically acceptable salts.

11. The method according to claim 1, wherein said compound is selected from the group consisting of:

(Z)-3-(2-(5-bromo-1H-indol-3-yl)-2-cyanovinyl)-4-methoxybenzonitrile; and (E)-3-(2-(5-bromo-1H-indol-3-yl)-2-cyanovinyl)-4-methoxybenzonitrile;

and their pharmaceutically acceptable salts.

12. A method for treating endometriosis in a subject in need thereof, comprising administering an effective amount of a pharmaceutical composition comprising a compound of formula (I):

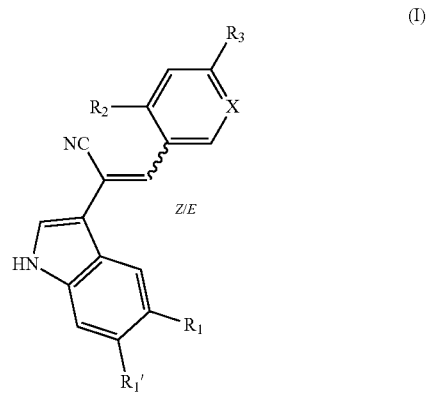

wherein:

X represents a nitrogen atom, a C—CN unit or a N+—O— unit;

$R_1$ and $R_1'$ represent independently H, a halogen, a hydroxy, an amino, or a $(C_1-C_6)$alkoxy group, optionally substituted by a carboxylic group or one —$NR_{11}R_{12}$ unit wherein $R_{11}$ and $R_{12}$ represent H, a $(C_1-C_6)$alkyl group, or $R_{11}$ and $R_{12}$ taken together form a 3- to 7-membered ring, optionally interrupted by one or several heteroatoms;

$R_2$ represents:
  a radical $(C_1-C_3)$alkyl, $(C_1-C_6)$alkoxy, $(C_3-C_6)$cycloalkoxy, aryloxy, heteroaryloxy, $(C_1-C_6)$alkyl-aryloxy, $(C_1-C_6)$alkyl-heteroaryloxy, said radicals being optionally substituted by at least one halogen, or a radical thio-$(C_1-C_6)$alkyl, thio-aryl, thio-heteroaryl, thio-$(C_1-C_6)$alkyl-aryl or thio-$(C_1-C_6)$-alkyl-heteroaryl, said radicals being optionally substituted by at least one halogen or by a $(C_1-C_6)$alkoxy group,
  a —$NR_4R_5$ unit, a O—$(C_1-C_6)$alkyl-$NR_4R_5$ unit or a S—$(C_1-C_6)$alkyl-$NR_4R_5$ unit wherein $R_4$ and $R_5$ represent H, a $(C_1-C_6)$alkyl group, or $R_4$ and $R_5$ taken together form a 3- to 7-membered ring, optionally interrupted by one or several heteroatoms, with the proviso that at least one among $R_4$ and $R_5$ is not H,
  a $NHCOR_6$ unit wherein $R_6$ represents $(C_1-C_6)$alkyl group,
  an aryl or heteroaryl group optionally substituted by at least one halogen, a trifluoromethyl group, or a $(C_1-C_3)$alkoxy group,
  a halogen, or
  a hydroxy; and $R_3$ represents a hydrogen, a $(C_1-C_3)$alkyl group, a $(C_1-C_3)$alkoxy group or a halogen;

and the compounds of formula (I) as above defined, in which the nitrogen atom of the indole core is substituted by a group selected from the group consisting of a $COR_7$ and a $CO_2R_7$ group, wherein $R_7$ represents:

a $(C_1-C_6)$alkyl group, optionally substituted by at least a hydroxy group, a $(C_1-C_6)$alkyloxy group, a $(C_1-C_6)$polyalkyloxy group wherein n is 1<n<6, a phosphate or pyrophosphate group and salts or $(C_1-C_3)$ alkyl ester thereof, a $R_8$ group, a —$NHCO_2R_8$ unit, a $COR_8$ group, or a $CO_2R_8$ group, wherein $R_8$ is:
  a $(C_1-C_6)$alkyl group;
  an aryl, a $(C_1-C_6)$alkylaryl, or a heteroaryl;
  a —$NR_9R_{10}$ unit wherein $R_9$ and $R_{10}$ represent a hydrogen, a $(C_1-C_6)$alkyl group, or $R_9$ and $R_{10}$ taken together form a 3- to 7-membered ring, optionally interrupted by one or several heteroatoms, and optionally the ring being substituted by at least one $(C_1$-$C_6)$alkyl group;

a NH—NR$_9$R$_{10}$ unit wherein R$_9$ and R$_{10}$ are as defined above; or a saturated heterocycle or a heteroaryl;

or one of its pharmaceutically acceptable salts.

13. The method according to claim 12, wherein said pharmaceutical composition further comprises an additional anti-endometriosis drug.

14. The method according to claim 12, wherein said pharmaceutical composition further comprises an additional anti-endometriosis drug selected from the group consisting of nonsteroidal anti-inflammatory drugs (NSAIDs), opioids, hormonal contraceptives drugs, growth factor inhibitors, endogenous angiogenesis inhibitors, fumagillin analogues, statins, cyclo-oxygenase-2 inhibitors, phytochemical compounds, immunomodulators, dopamine agonists, peroxisome proliferator-activated receptor agonists, progestins, danazol, and gonadotropin-releasing hormone agonists.

* * * * *

UNITED STATES PATENT AND TRADEMARK OFFICE
CERTIFICATE OF CORRECTION

PATENT NO. : 10,624,876 B2  
APPLICATION NO. : 16/344390  
DATED : April 21, 2020  
INVENTOR(S) : Philippe Pouletty Page 1 of 1

It is certified that error appears in the above-identified patent and that said Letters Patent is hereby corrected as shown below:

In the Specification

Column 26,
Line 1, "DO." should read --D0.--.

Signed and Sealed this  
Twenty-fifth Day of August, 2020

Andrei Iancu  
*Director of the United States Patent and Trademark Office*